United States Patent
Henschke et al.

(10) Patent No.: US 8,999,941 B2
(45) Date of Patent: Apr. 7, 2015

(54) CRYSTALLINE AND NON-CRYSTALLINE FORMS OF SGLT2 INHIBITORS

(71) Applicant: ScinoPharm Taiwan, Ltd., Shan-Hua (TW)

(72) Inventors: Julian Paul Henschke, Summertown (AU); Meng-Fen Ho, Tainan (TW); Shu-Ping Chen, Kaohsiung (TW); Yung-Fa Chen, Tainan (TW)

(73) Assignee: ScinoPharm Taiwan, Ltd., Shan-Hua (TW)

( * ) Notice: Subject to any disclaimer, the term of this patent is extended or adjusted under 35 U.S.C. 154(b) by 101 days.

(21) Appl. No.: 13/664,380

(22) Filed: Oct. 30, 2012

(65) Prior Publication Data

US 2013/0237487 A1 Sep. 12, 2013

Related U.S. Application Data

(60) Provisional application No. 61/553,776, filed on Oct. 31, 2011.

(51) Int. Cl.
*C07D 409/10* (2006.01)
*C07D 409/00* (2006.01)

(52) U.S. Cl.
CPC ............ *C07D 409/10* (2013.01); *C07D 409/00* (2013.01)

(58) Field of Classification Search
None
See application file for complete search history.

(56) References Cited

U.S. PATENT DOCUMENTS

| | | | |
|---|---|---|---|
| 6,774,112 | B2 | 8/2004 | Gougoutas |
| 2008/0146515 | A1 | 6/2008 | Nomura et al. |
| 2009/0143316 | A1 | 6/2009 | Imamura et al. |
| 2009/0233874 | A1 | 9/2009 | Abdel-Magid et al. |
| 2011/0087017 | A1 | 4/2011 | Farina et al. |
| 2011/0098240 | A1 | 4/2011 | Dugi et al. |
| 2012/0289694 | A1* | 11/2012 | Nguyen et al. ................ 536/122 |

FOREIGN PATENT DOCUMENTS

WO 2008/002824 A1 1/2008

OTHER PUBLICATIONS

PCT/IB2012/002852 International Search Report and Written Opinion, mailed Jun. 21, 2013 8 pages.

* cited by examiner

*Primary Examiner* — Layla Bland
(74) *Attorney, Agent, or Firm* — Kilpatrick Townsend & Stockton LLP

(57) ABSTRACT

The present invention provides amorphous forms and the crystalline complexes of SGLT2 inhibitors as a novel material, in particular in pharmaceutically acceptable form. The crystalline forms of SGLT2 inhibitor canagliflozin are designated as Forms CS1, CS2, CS3, CS4 and CS5.

10 Claims, 26 Drawing Sheets

CRYSTALLINE AND NON-CRYSTALLINE FORMS OF SGLT2 INHIBITORS

CROSS-REFERENCES TO RELATED APPLICATIONS

This application claims the benefit of priority to U.S. Provisional Application Ser. No. 61/553,776, filed Oct. 31, 2011, the entire content of which is incorporated herein by reference.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Diabetes mellitus is a serious and chronic metabolic disease that is characterized by high blood glucose (hyperglycemia) and affects millions of people world-wide. SGLT2 is a Sodium-dependent GLucose co-Transporter protein which affects the reabsorption of glucose in the kidney. It is estimated that 90% of renal glucose reabsorption is facilitated by SGLT2. Since glucose reabsorption is mediated predominantly by SGLT2 and because high glucose levels have been identified as a cause of disease in diabetes, SGLT2 has become a drug target for type 2 diabetes therapy. Selective inhibition of SGLT2 has the potential to reduce hyperglycemia by inhibiting glucose reabsorption in the kidney with elimination of glucose by excretion in the urine (glucosuria).

Dapagliflozin (trade name: Forxiga) is an active pharmaceutical ingredient (API) and a selective inhibitor of SGLT2 that is being developed for the treatment of type 2 diabetes mellitus. Marketing approval for dapagliflozin is being sought.

The IUPAC systematic name of dapagliflozin is (2S,3R,4R,5S,6R)-2-[4-chloro-3-(4-ethoxybenzyl)phenyl]-6-(hydroxymethyl)tetrahydro-2H-pyran-3,4,5-triol, and is also known as (1S)-1,5-anhydro-1-C-{4-chloro-3-[(4-ethoxyphenyl)methyl]phenyl}-D-glucitolI. Dapagliflozin is a white to off-white powder with a molecular formula of $C_{21}H_{25}ClO_6$ and a molecular weight of 408.87. The structure of dapagliflozin is shown as compound A.

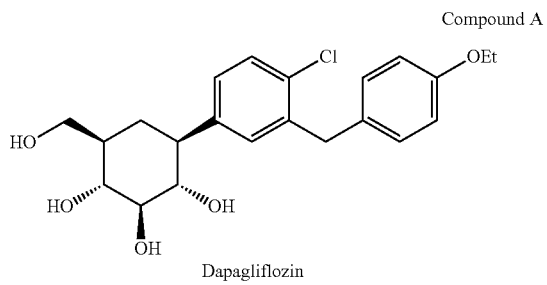 [SMILES: CCOc1ccc(Cc2cc([C@@H]3C[C@H](CO)[C@@H](O)[C@H](O)[C@H]3O)ccc2Cl)cc1]

Compound A

Dapagliflozin

In U.S. Pat. No. 6,774,112 B2, crystalline complexes formed from both the D- or L-enantiomers of natural amino acids and SGLT2 inhibitors are disclosed.

In PCT application WO 2008/002824 A1, crystalline forms of dapagliflozin comprising (S)-propylene glycol (PG), (R)-PG, EtOH, ethylene glycol (EG), 1:2 L-proline, 1:1 L-proline, 1:1 L-proline hemihydrate, and 1:1 L-phenylalanine are disclosed.

Processes for preparing some of the aforesaid crystalline foiins comprising dapagliflozin and various alcohols and diols are also disclosed in the PCT application WO 2008/002824 A1.

Canagliflozin is an API that is an inhibitor of SGLT2 and is being developed for the treatment of type 2 diabetes mellitus.

The IUPAC systematic name of canagliflozin is (2S,3R,4R,5S,6R)-2-{3-[5-[4-fluorophenyl)-thiophen-2-ylmethyl]-4-methyl-phenyl}-6-hydroxymethyl-tetrahydro-pyran-3,4,5-triol, and is also known as (1S)-1,5-anhydro-1-C-[3-[[5-(4-fluorophenyl)-2-thienyl]methyl]-4-methylphenyl]-D-glucitol and 1-(β-D-glucopyranosyl)-4-methyl-3-[5-(4-fluorophenyl)-2-thienylmethyl]henzene. Canagliflozin is a white to off-white powder with a molecular formula of $C_{24}H_{25}FO_5S$ and a molecular weight of 444.52. The structure of canagliflozin is shown as compound B.

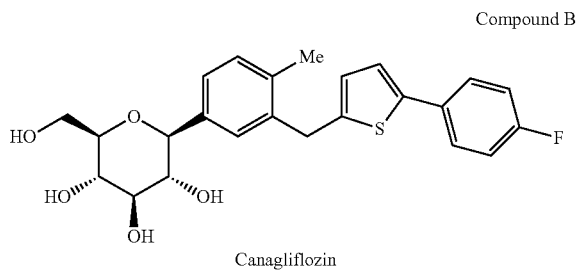 [SMILES: Cc1ccc([C@@H]2O[C@H](CO)[C@@H](O)[C@H](O)[C@H]2O)cc1Cc1ccc(-c2ccc(F)cc2)s1]

Compound B

Canagliflozin

In US 2008/0146515 A1, a crystalline hemihydrate form of canagliflozin (shown as Compound C) is disclosed, having the powder X-ray diffraction (XRPD) pattern comprising the following 2θ values measured using CuKα radiation: 4.36±0.2, 13.54±0.2, 16.00±0.2, 19.32±0.2, and 20.80±0.2. The XRPD pattern is shown in FIG. 24. A process for the preparation of canagliflozin hemihydrate is also disclosed in U.S. 2008/0146515 A1.

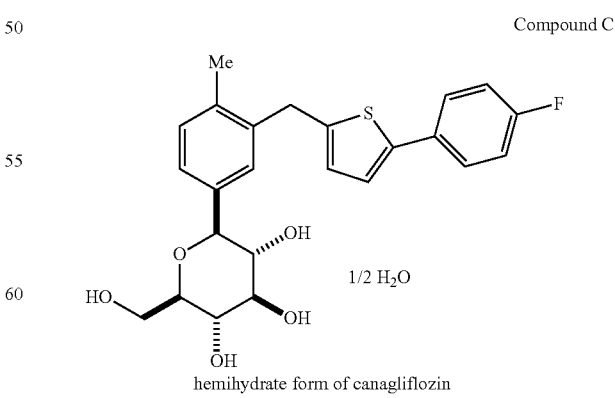

Compound C hemihydrate form of canagliflozin

In US 2009/0233874 A1, a crystalline form of canagliflozin is disclosed. FIG. 25 shows the XRPD pattern of the crystalline form in the detailed description, and the characterized XRPD pattern peaks are shown in Table 1 below.

TABLE 1

The characterized XRPD pattern peaks of canagliflozin form

| Position (2° theta) | d-spacing (Å) |
|---|---|
| 3.9 | 22.8 |
| 8.0 | 11.1 |
| 9.7 | 9.2 |
| 10.9 | 8.1 |
| 13.0 | 6.8 |
| 13.9 | 6.4 |
| 15.5 | 5.7 |
| 15.6 | 5.7 |
| 15.9 | 5.6 |
| 16.2 | 5.5 |
| 17.3 | 5.1 |
| 18.3 | 4.9 |
| 18.7 | 4.7 |
| 18.8 | 4.7 |
| 19.1 | 4.6 |
| 19.4 | 4.6 |
| 20.3 | 4.4 |
| 20.9 | 4.3 |
| 21.1 | 4.2 |
| 21.8 | 4.1 |
| 22.5 | 3.9 |
| 22.7 | 3.9 |
| 23.2 | 3.8 |
| 23.4 | 3.8 |
| 25.1 | 3.6 |
| 25.7 | 3.5 |
| 26.3 | 3.4 |
| 26.8 | 3.3 |
| 27.3 | 3.3 |

BRIEF SUMMARY OF THE INVENTION

The present invention provides novel crystalline complexes and amorphous forms of SGLT2 inhibitors, and processes for the preparation of these forms. These crystalline complexes of SGLT2 inhibitors are designated as Forms CS1, CS2, CS3, CS4 and CS5.

The above mentioned amorphous forms and crystalline complexes have all been chemically characterized by $^1$H NMR (nuclear magnetic resonance) spectroscopy, $^{13}$C NMR spectroscopy, XRPD (X-ray powder diffraction) analysis, FTIR (Fourier transform infrared) spectroscopy, TGA (thermogravimetric analysis) analysis and DSC (differential scanning calorimetry) analysis.

Also included in the present invention are methods for preparing the crystalline complex forms, amorphous forms as well as pharmaceutical preparations of the aforesaid forms.

DETAILED DESCRIPTION OF THE INVENTION

Figure 1:
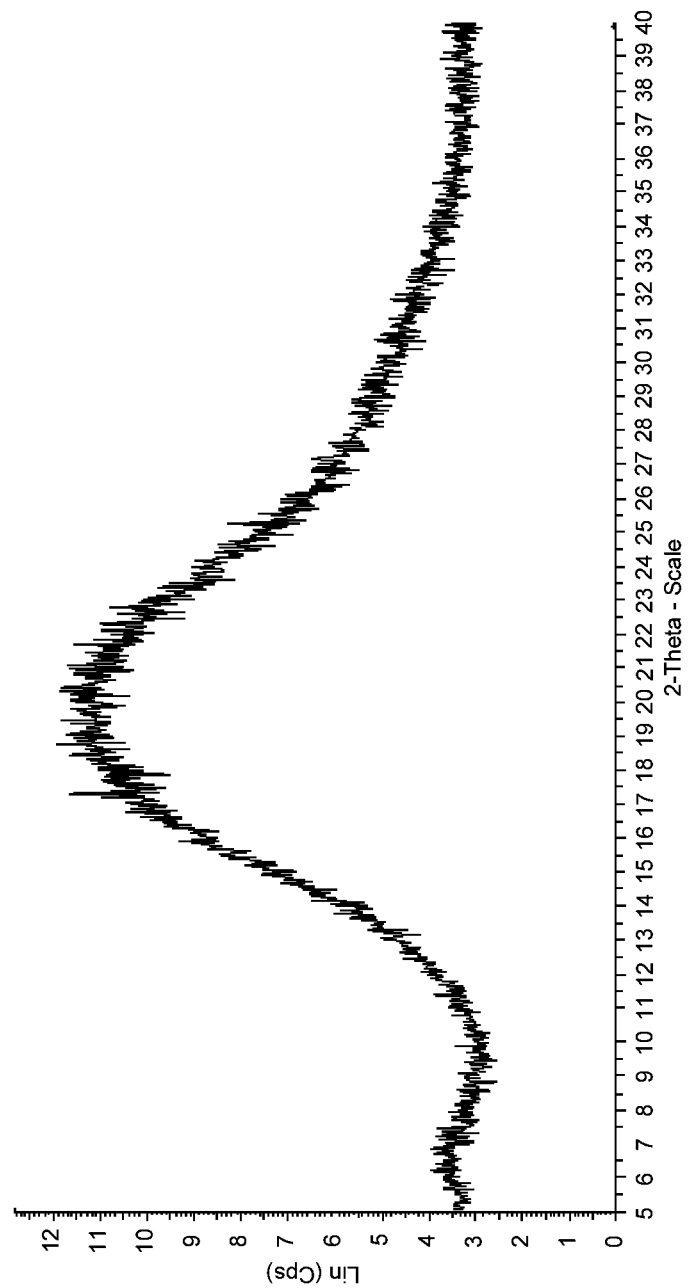
FIGS. 1 and 2 provide the XRPD pattern and IR spectrum, respectively, of amorphous dapagliflozin.

The present invention provides an amorphous form of dapagliflozin and canagliflozin, as well as new crystalline complexes of canagliflozin as novel materials, suitable for pharmaceutical preparations. These crystalline complexes and amorphous forms can be produced by the methods described herein and are substantially free of other crystalline forms. The term "substantially free" refers to an amount of 10% or less of another form, preferably 8%, 5%, 4%, 3%, 2%, 1%, 0.5%, or less of another form.

In one aspect, the present invention provides an amorphous form of (2S,3R,4R,5S,6R)-2-[4-chloro-3-(4-ethoxybenzyl)phenyl]-6-(hydroxymethy)tetrahydro-2H-pyran-3,4,5-triol (dapagliflozin).

In another aspect, the present invention provides an amorphous form of (2S,3R,4R,5S,6R)-2-{3-[5-[4-fluoro-phenyl)-thiophen-2-ylmethyl]-4-methyl-phenyl}-6-hydroxymethyl-tetrahydro-pyran-3,4,5-triol (canagliflozin).

In yet another aspect, the present invention provides crystalline complexes of (2S,3R,4R,5S,6R)-2-{3-[5-[4-fluoro-phenyl)-thiophen-2-ylmethyl]-4-methyl-phenyl}-6-hydroxymethyl-tetrahydro-pyran-3,4,5-triol (canagliflozin).

The amorphous forms and crystalline complexes of the present invention can be characterized by X-ray powder diffraction (XRPD) analysis, infrared (IR) spectroscopy, differential scanning calorimetry (DSC) traces, thermal gravimetric analysis (TGA), and the unit cell of the crystal structure for the crystalline complexes.

In some embodiments, the present invention provides the amorphous forms and crystalline complexes of the SGLT2 inhibitors characterized by the XRPD substantially in accordance with that of FIG. 1, 3, 5, 10, 15, 20 or 22.

In other embodiments, the present invention provides an amorphous form of dapagliflozin. XRPD analysis confirmed that the material was amorphous as indicated by the lack of any peaks, and this was supported by SEM (scanning electron microscopy) which showed that the material consisted of irregular particles. The amorphous form of dapagliflozin is characterized by the XRPD pattern in accordance with FIG. 1.

The amorphous, solid dapagliflozin was prepared by adding its heated toluene solution into n-heptane. After drying in vacuo the product was obtained as a white solid of with melting point of 49.5° C. to 62.6° C.

TGA analysis of the amorphous dapagliflozin of this invention showed some mass loss upon heating. DSC analysis showed the existence of two endothermic transitions at 57° C. and 107° C. which were indicative of dehydration and solvent evaporation.

In other embodiments, the present invention provides an amorphous form of canagliflozin. The amorphous form of canagliflozin is characterized by the XRPD pattern in accordance with FIG. 3.

The amorphous, solid canagliflozin was prepared by adding its heated toluene solution into n-heptane. After drying in vacuo the product was obtained as a white solid with melting point of 54.7° C. to 72.0° C. Dynamic vapor sorption (DVS) analysis of the amorphous form of canagliflozin (FIG. 26) indicates that the form was hygroscopic. Moreover, from the DVS isotherm plots (FIG. 27; change is mass versus target relative humidity) it was seen that the second sorption/desorption cycle was different from the first cycle. Further experimentation and observations indicated that the amorphous form underwent a physical change between the sorption/desorption cycle, making the sorption/desorption behavior different between the two cycles. The physical change that occurred was determined to be a conversion or partial conversion from the amorphous state to a crystalline state. This was supported by a change in the overall appearance of the sample as the humidity increased from 70% to 90% RH, the measurement of a gradual decrease in mass while being held at 90% RH for an extended period of time, and the detection of birefringence when inspecting particles (following the DVS study where the sample was held at 90% RH) under a microscope with a polarizing filter.

In other embodiments, the present invention provides a crystalline complex of canagliflozin with L-proline (Form CS1). The XRPD pattern of Form CS1 shows that it is crystalline, as is also indicated by SEM. Form CS1 was shown to be different from the amorphous form of canagliflozin by XRPD analysis. The crystalline complex Form CS1 of canagliflozin is characterized by the XRPD pattern in accordance with FIG. 5. In some embodiments, the crystalline form of the compound is characterized by an XRPD pattern that includes two or more, three or more, four or more, or five or more peaks selected from peaks at 8.92, 9.47, 10.29, 10.9, 11.38, 12.63, 13.18, 14.57, 15.4, 16.08, 17.02, 17.69, 17.9, 18.62, 19.06, 19.89, 20.28, 20.83, 21.23, 21.85, 22.56, 22.95, 23.44, 24.11, 24.57, 25.48, 25.91, 26.84, 27.7, 28.1, 28.75, 29.84, 30.41, 30.86, 31.3, 31.63, 32.21, 33.67, 34.47, 35.1, 35.91 and 36.37 degrees 2θ (±0.1 degrees 2θ), wherein said XRPD pattern is made using CuK$_{\alpha 1}$ radiation. In some other embodiments, the crystalline form of the compound is characterized by an XRPD pattern that includes peaks (in degrees 2θ (±0.1 degrees 2θ)) as provided in FIG. 5 that are greater than 20 Cps. In other embodiments, the crystalline form of the compound is characterized by the XRPD peaks substantially in accordance with FIG. 5.

Figure 8:
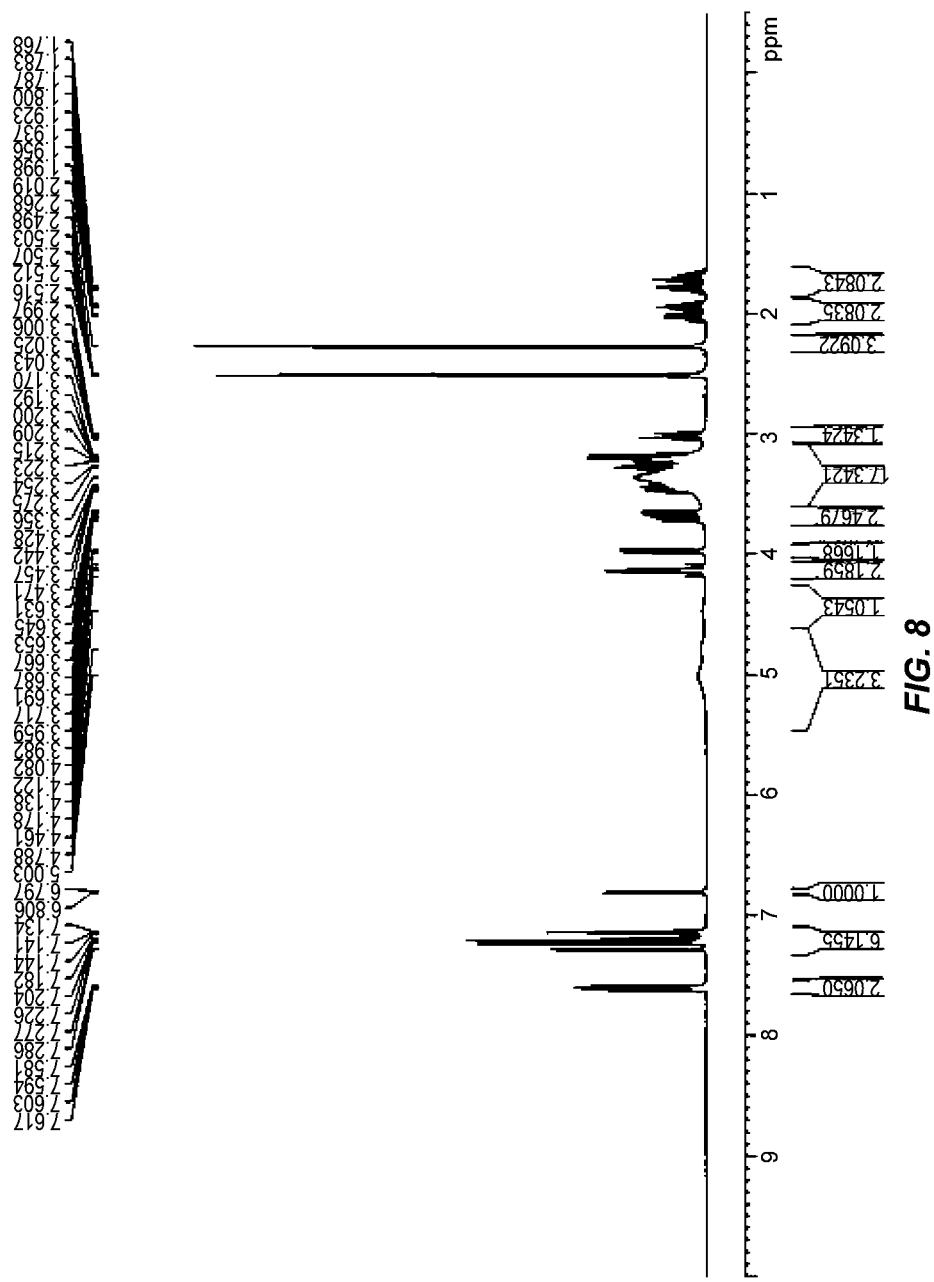
Figure 9:
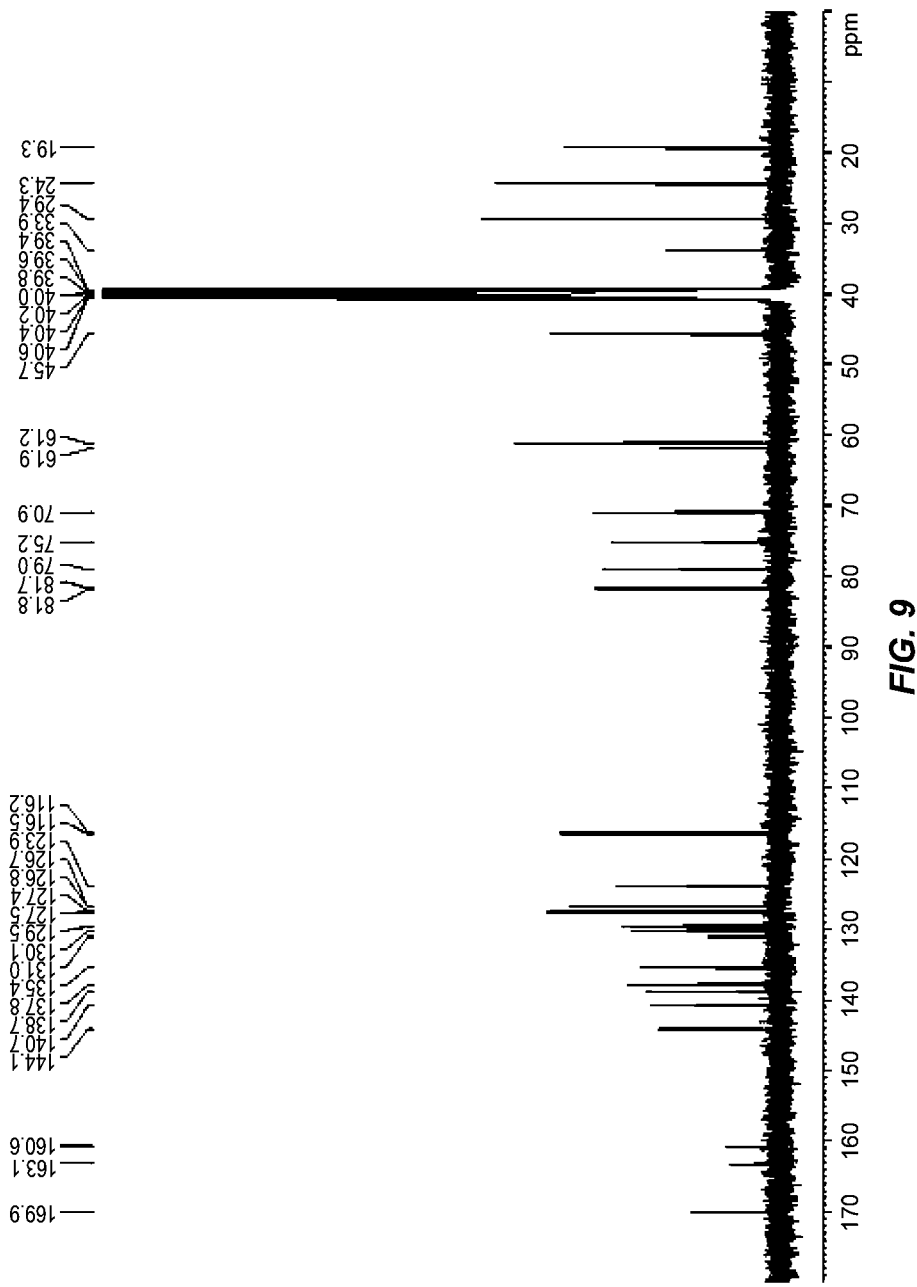

Crystallization of canagliflozin from aqueous ethanol (EtOH) in the presence of the natural amino acid L-proline provided solids that after drying in vacuo furnished a white solid with a melting starting at about 188° C. FIG. 8 is the $^1$H NMR spectrum of Form CS1, showing that it comprises canagliflozin with L-proline in a 1:1 molar ratio.

Figure 7:
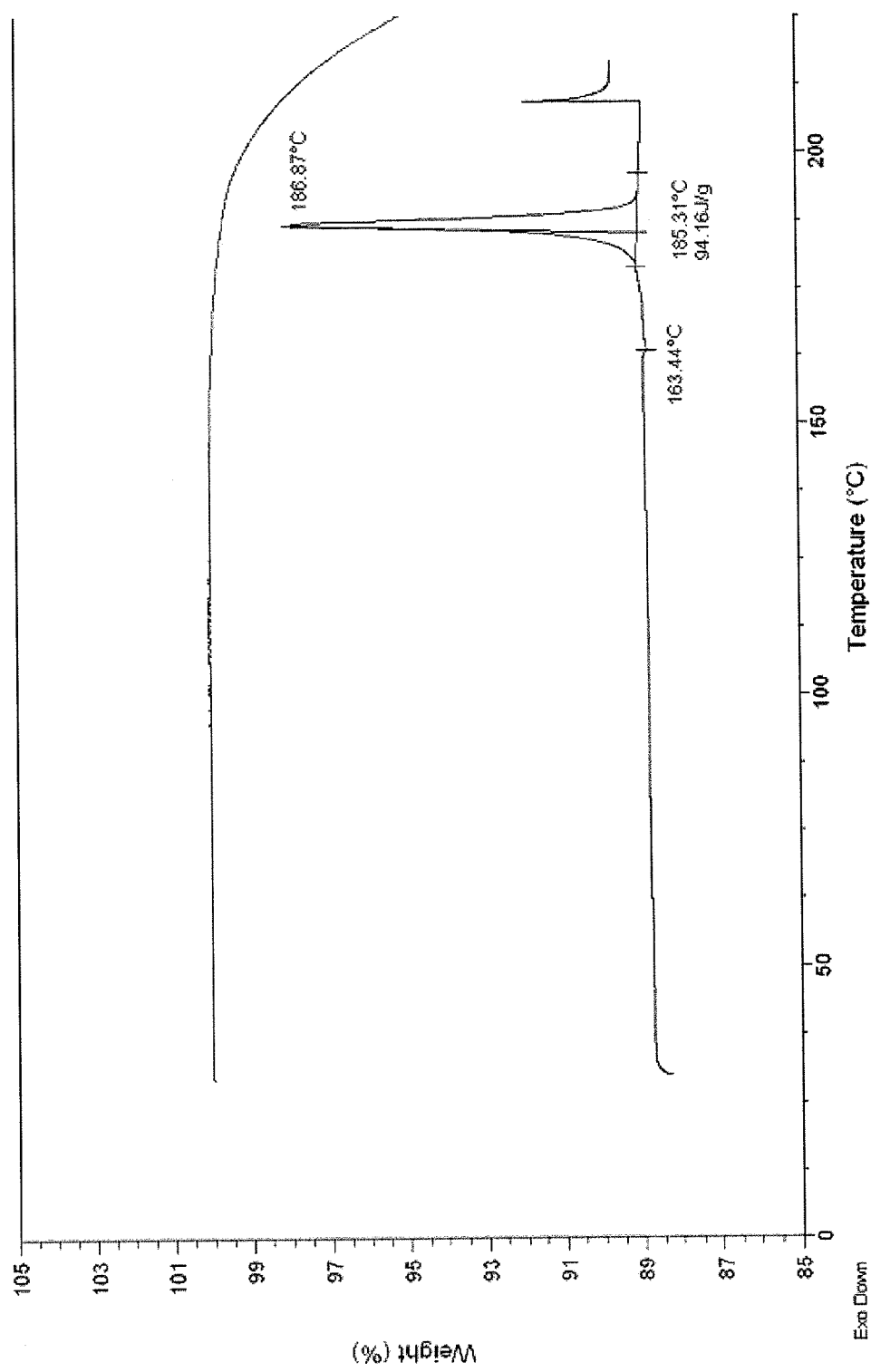
FIGS. 7, 8 and 9 provide DSC and TGA traces, $^1$H NMR and $^{13}$C NMR spectra, respectively, of a 1:1 crystalline complex of canagliflozin with L-proline (Form CS1).

Form CS1 has been further characterized using DSC/TGA and Karl Fischer titration. The TGA curve shows no significant mass loss at a temperature below 150° C., which indicates Form CS1 is an anhydrous and non-solvated material. The TGA analysis result is consistent with the Karl Fischer titration analysis result which shows the water content of material exposed to the laboratory environment was less than 0.5%. DSC analysis showed an endothermic transition at about 180° C. to 190° C., with the peak maximum at about 189° C., and HSM (hot stage microscopy) analysis confirmed that this thermal event corresponded to sample melting. The DSC/TGA traces of crystalline complex Form CS1 of canagliflozin is in accordance with FIG. 7.

Figure 26:
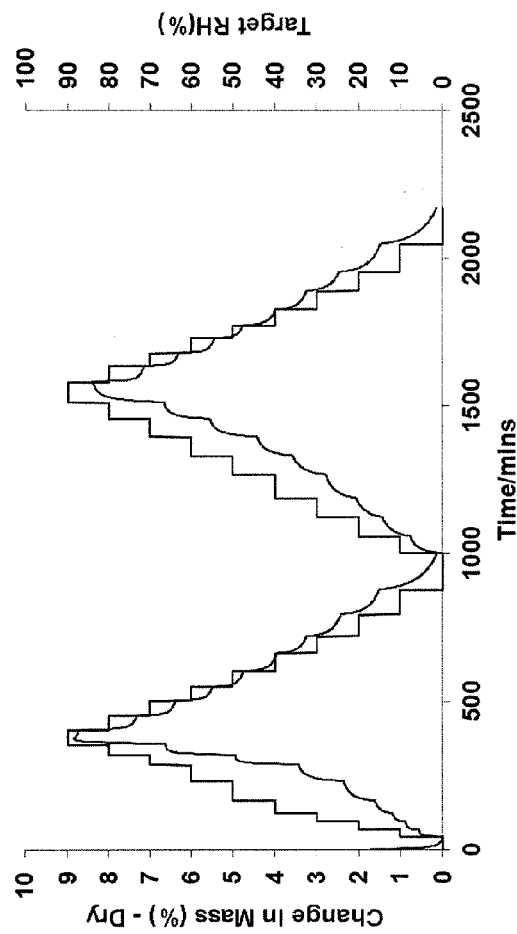
FIG. 26 provides the dynamic vapor sorption (DVS) plot for the amorphous form of canagliflozin, showing mass change as a percentage as a function of time and relative humidity as a function of time.
Figure 27:
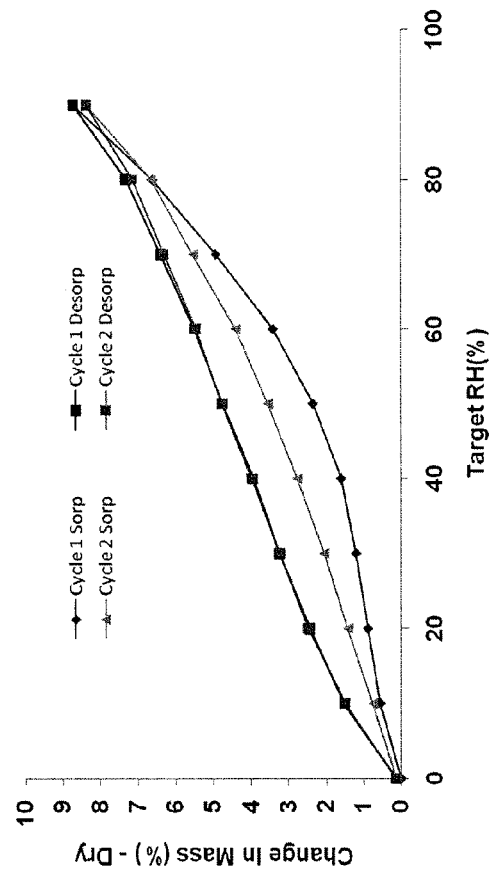
FIG. 27 provides the dynamic vapor sorption (DVS) isotherm plots for the amorphous form of canagliflozin, showing change is mass versus target relative humidity.
Figure 28:
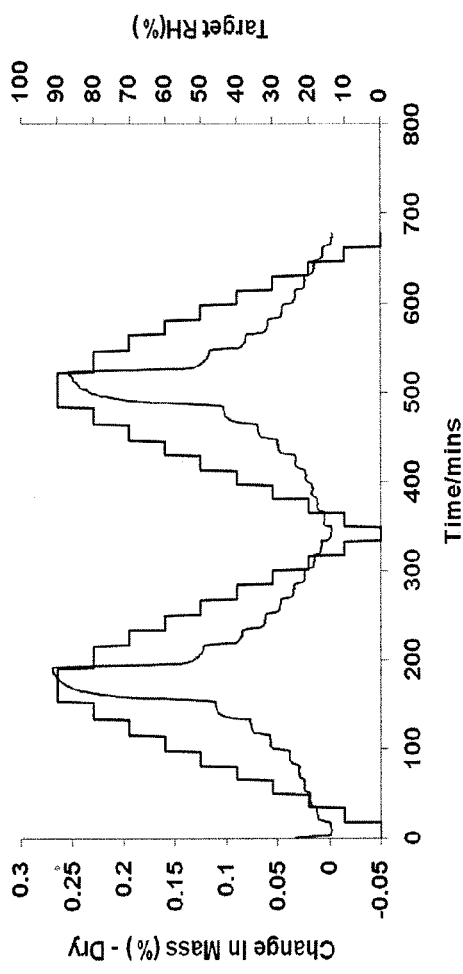
FIG. 28 provides the dynamic vapor sorption (DVS) plot for the crystalline complex Form CS1 of canagliflozin, showing mass change as a percentage as a function of time and relative humidity as a function of time.
Figure 29:
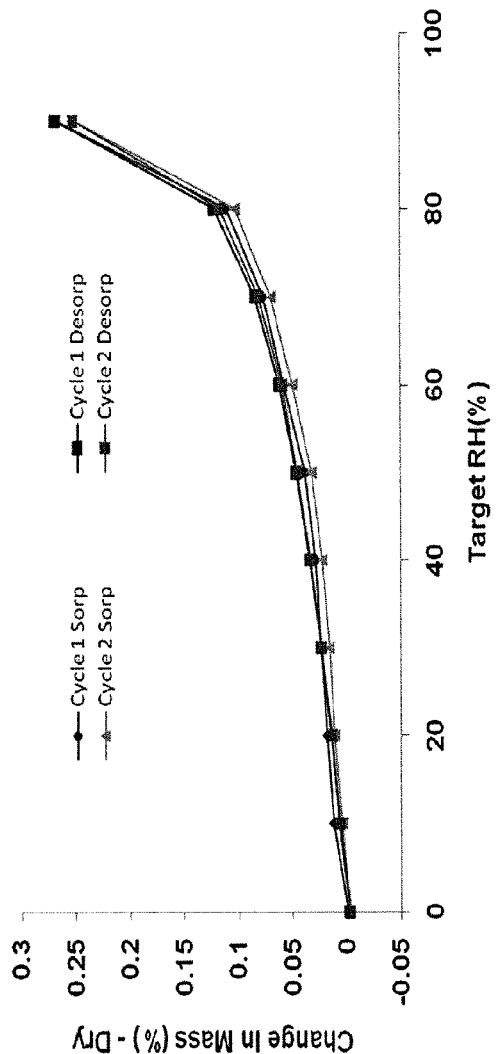
FIG. 29 provides the dynamic vapor sorption (DVS) isotherm plots for the crystalline complex Form CS1 of canagliflozin, showing mass change as a percentage as a function of time and relative humidity as a function of time.

Dynamic vapor sorption (DVS) analysis of the crystalline complex Form CS1 of canagliflozin (FIG. 28) indicates that the crystalline form is not hygroscopic, in contrast to the amorphous form of canagliflozin which was shown to be significantly hygroscopic (FIG. 26). That is, unlike the amorphous form of canagliflozin, the sample did not show significant moisture sorption when the relative humidity was increased from 0% to 90%. The small mass increase seen upon humidification represents adsorptions of moisture to the surface of the crystals rather than incorporation into the crystal lattice. Analysis of the DVS isotherm plots (FIG. 29; change is mass versus target relative humidity) from two sorption/desorption cycles of the crystalline complex Form CS1 of canagliflozin showed that the sorption/desorption behavior was completely consistent between cycles. That is the behavior is reversible and no indication of change in physical form occurs during sorption/desorption. This consistent sorption/desorption behavior contrasts with that of the amorphous form of canagliflozin that was found to be inconsistent between the two cycles tests (FIG. 27). One skilled in the art will recognize that the above described moisture sorption/desorption behavior of the crystalline complex Form CS1 of canagliflozin provides an advantage over that of the amorphous form. In particular, the crystalline complex Form CS1 of canagliflozin is stable in the presence or absence of moisture and retains its integrity, while the amorphous form of canagliflozin undergoes physical change (from amorphous to crystalline) as the humidity is changed. Thus, the physical stability of the crystalline complex Form CS1 of canagliflozin under different degrees of humidity provides advantages to the manufacturer and formulator as compared to the amorphous form of canagliflozin. Of the embodiments described, the crystalline complex Form CS1 of canagliflozin is the most preferred solid form of canagliflozin of this invention.

In other embodiments, the present invention is related to an EtOH solvate of a 1:1 crystalline complex of canagliflozin with D-proline (Form CS2). XRPD analysis and SEM showed that it was crystalline. Form CS2 was shown to be different from the amorphous form of canagliflozin and from Form CS1 by XRPD analysis. The crystalline complex Form CS2 of canagliflozin is characterized by an XRPD pattern in accordance with FIG. 10. In some embodiments, the crystalline form of the compound is characterized by an XRPD pattern that includes two or more, three or more, four or more, or five or more peaks selected from peaks at 8.13, 8.4, 9.08, 9.63, 10.95, 11.85, 12.88, 13.33, 14.37, 16.12, 16.86, 17.23, 18.02, 18.29, 18.88, 19.56, 20.35, 20.97, 21.67, 22.22, 22.89, 24.45, 25.14, 26.3, 26.59, 27.06, 27.54, 28.17, 28.58, 29.9, 30.79, 31.69, 32.89, 33.45, 33.7, 34.04, 35.38, 36.47, 37.0, 37.93, 38.43 and 39.37 degrees 2θ (±0.1 degrees 2θ), wherein said XRPD pattern is made using CuK$_{α1}$ radiation. In some other embodiments, the crystalline form of the compound is characterized by an XRPD pattern that includes peaks (in degrees 2θ (±0.1 degrees 2θ)) as provided in FIG. 10 that are greater than 20 Cps. In other embodiments, the crystalline form of the compound is characterized by the XRPD peaks substantially in accordance with FIG. 10.

Figure 13:
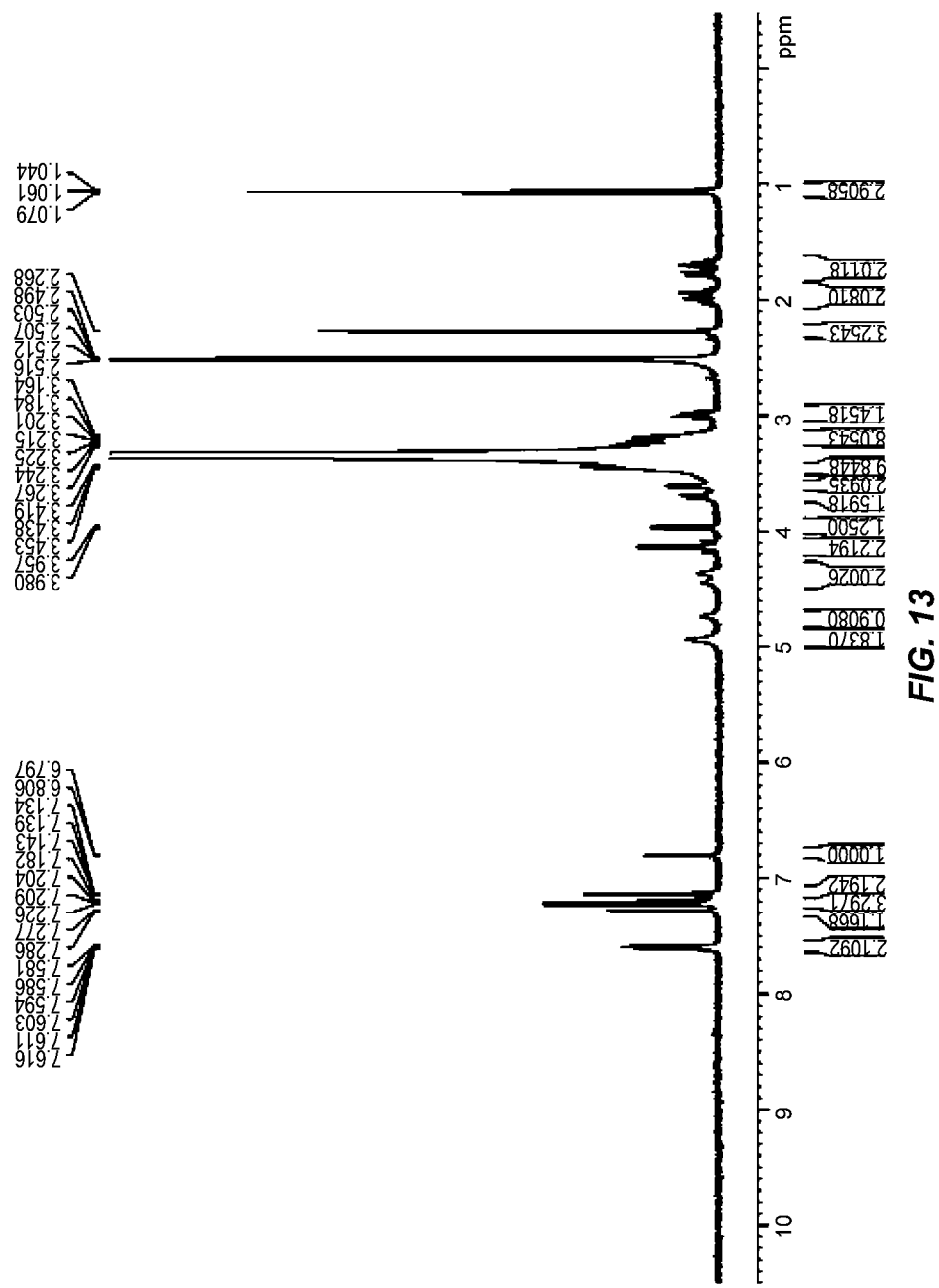
Figure 14:
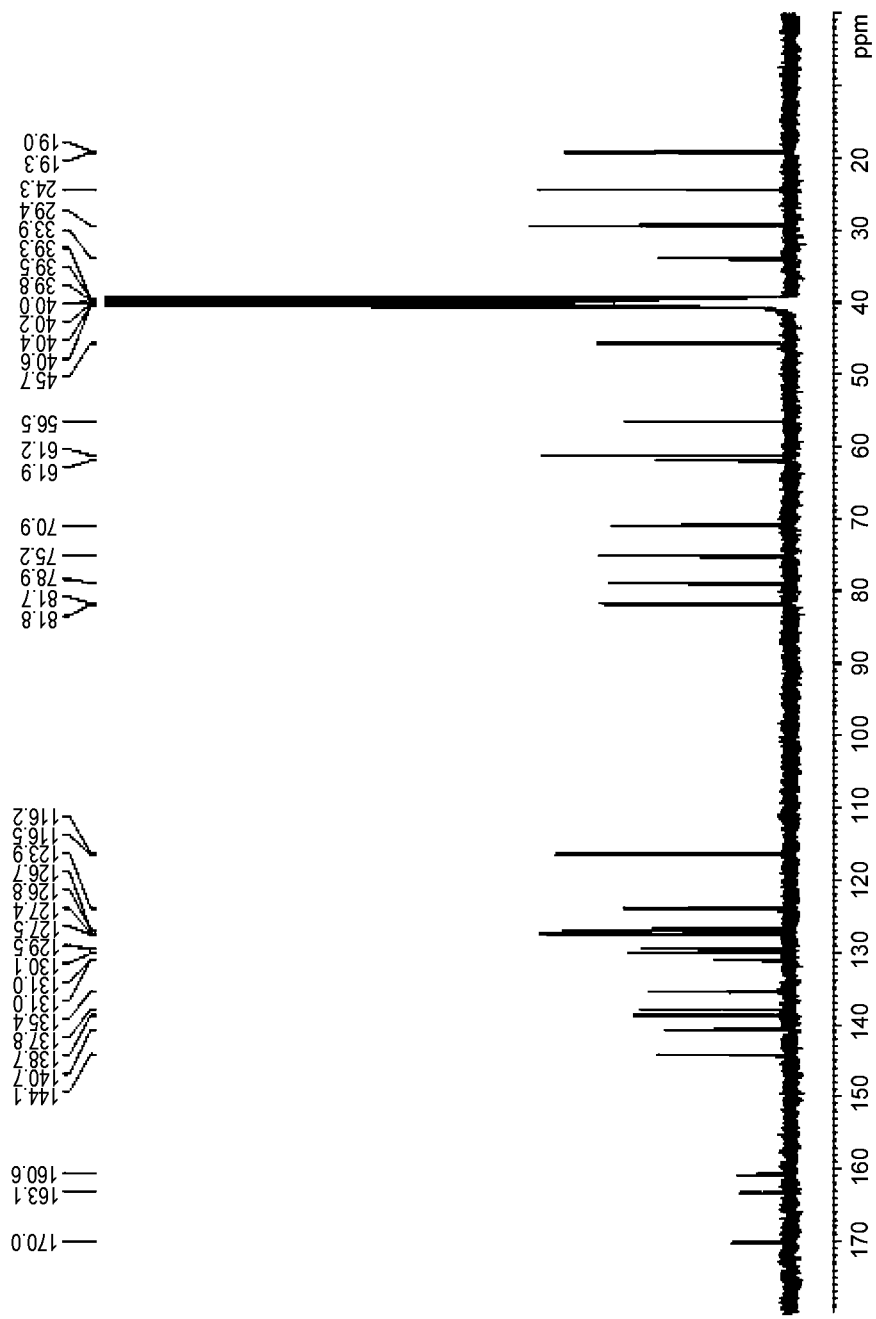

Crystallization of Form CS2 from aqueous EtOH in the presence of the amino acid D-proline provided solids that after drying in vacuo furnished a white solid. FIG. 13 is the $^1$H NMR spectrum of Form CS2, showing that it comprises canagliflozin and D-proline in a 1:1 molar ratio with about 0.4-0.6 molar equivalents of EtOH.

Figure 12:
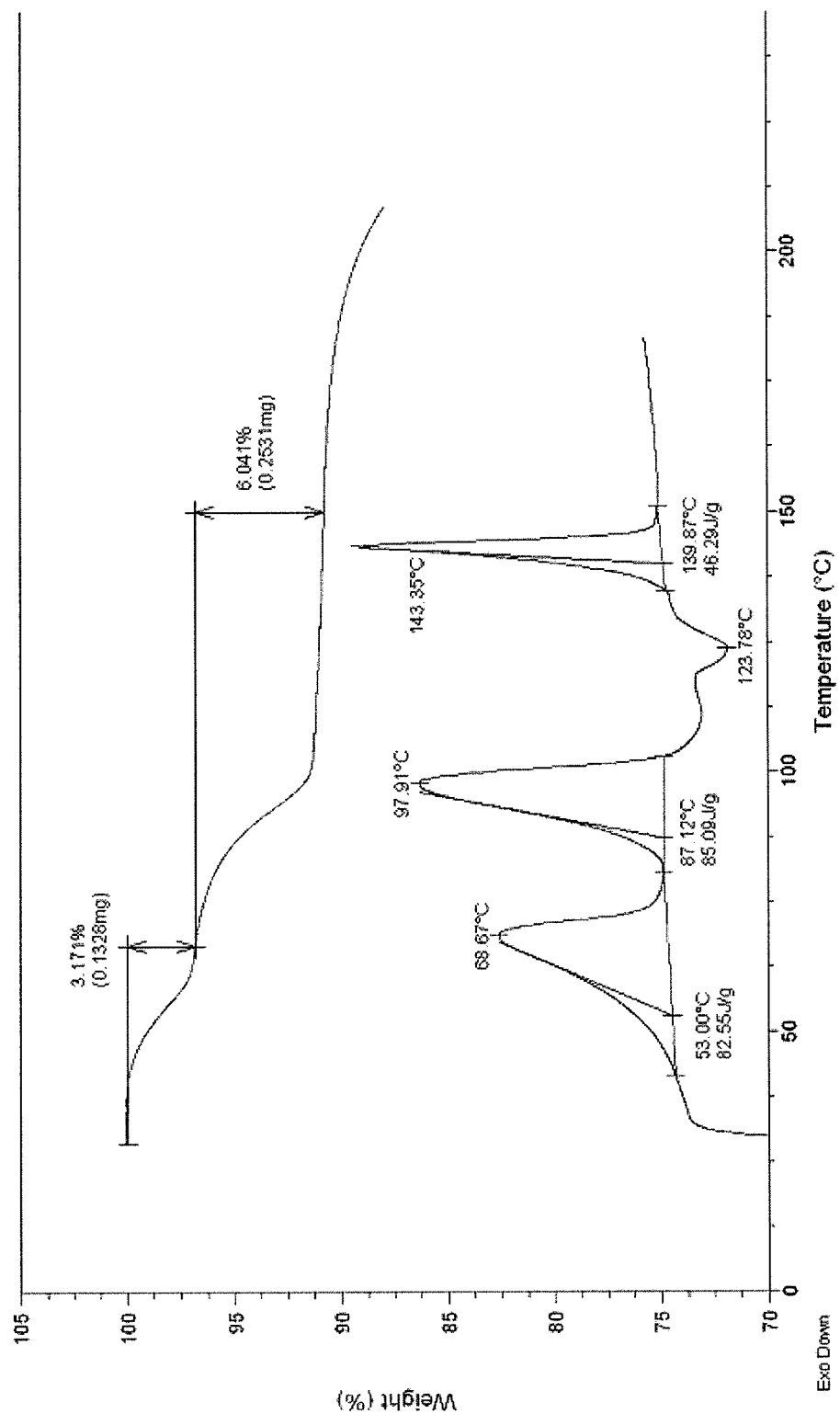
FIGS. 12, 13 and 14 provide the DSC and TGA traces, $^1$H NMR, and $^{13}$C NMR spectra, respectively, of an EtOH solvate of a 1:1 crystalline complex of canagliflozin with D-proline (Form CS2).

Form CS2 has been further characterized using DSC/TGA and Karl Fischer titration. TGA analysis shows two mass loss stages observed at about 50° C. and 90° C. with a mass loss of 3.2% and 6% respectively, which corresponds to the result obtained from Karl Fischer titration analysis and $^1$H NMR spectroscopic analysis, of about 3.5% water content and about 3% to 5% EtOH. Therefore, co-crystalline Form CS2 is a monohydrate, ethanol solvate. DSC analysis shows three endothermic transitions at about 69° C., 98° C. and 143° C. HSM analysis confirms that the first thermal event is dehydration and that the second one is ethanol evaporation, accompanied by partial sample melting. Complete melting occurred by about 145° C. DSC analysis also indicates that Form CS2 was different from D-proline and from canagliflozin. The DSC/TGA traces of crystalline complex Form CS2 of canagliflozin are in accordance with FIG. 12.

Figure 15:
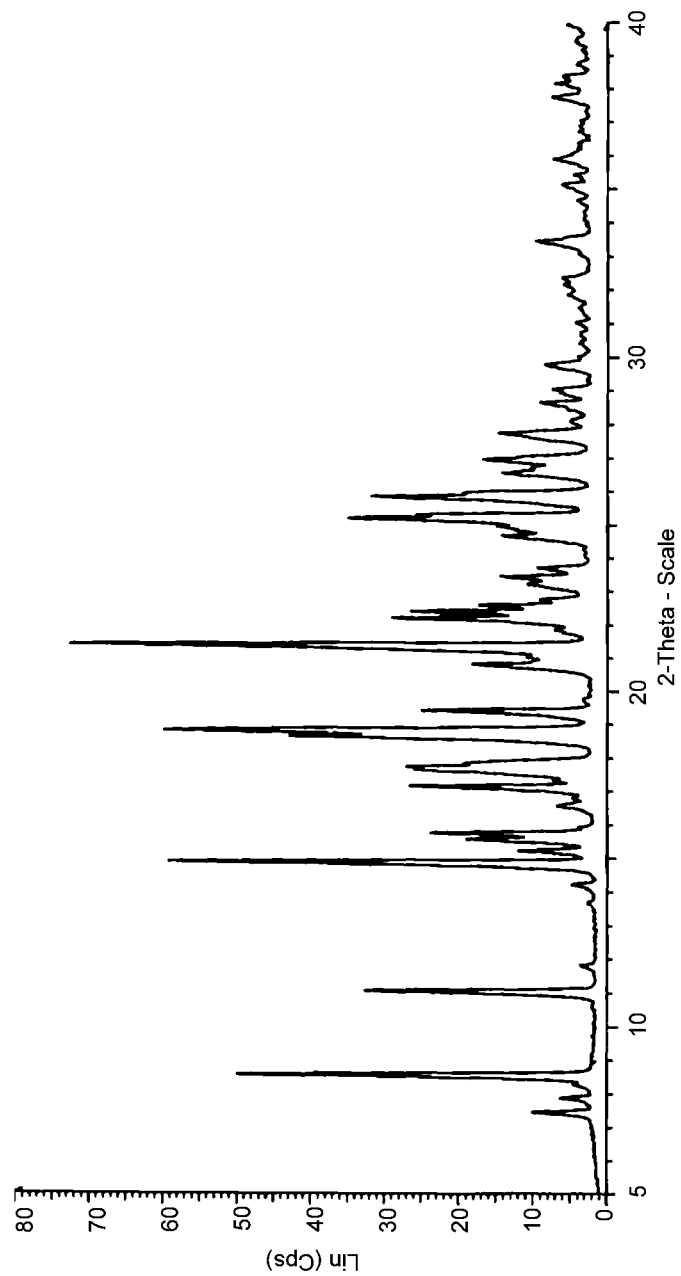
FIGS. 15 and 16 provide the XRPD pattern and IR spectrum, respectively, of 1:1 crystalline complex of canagliflozin and L-phenylalanine (Form CS3).
Figure 16:
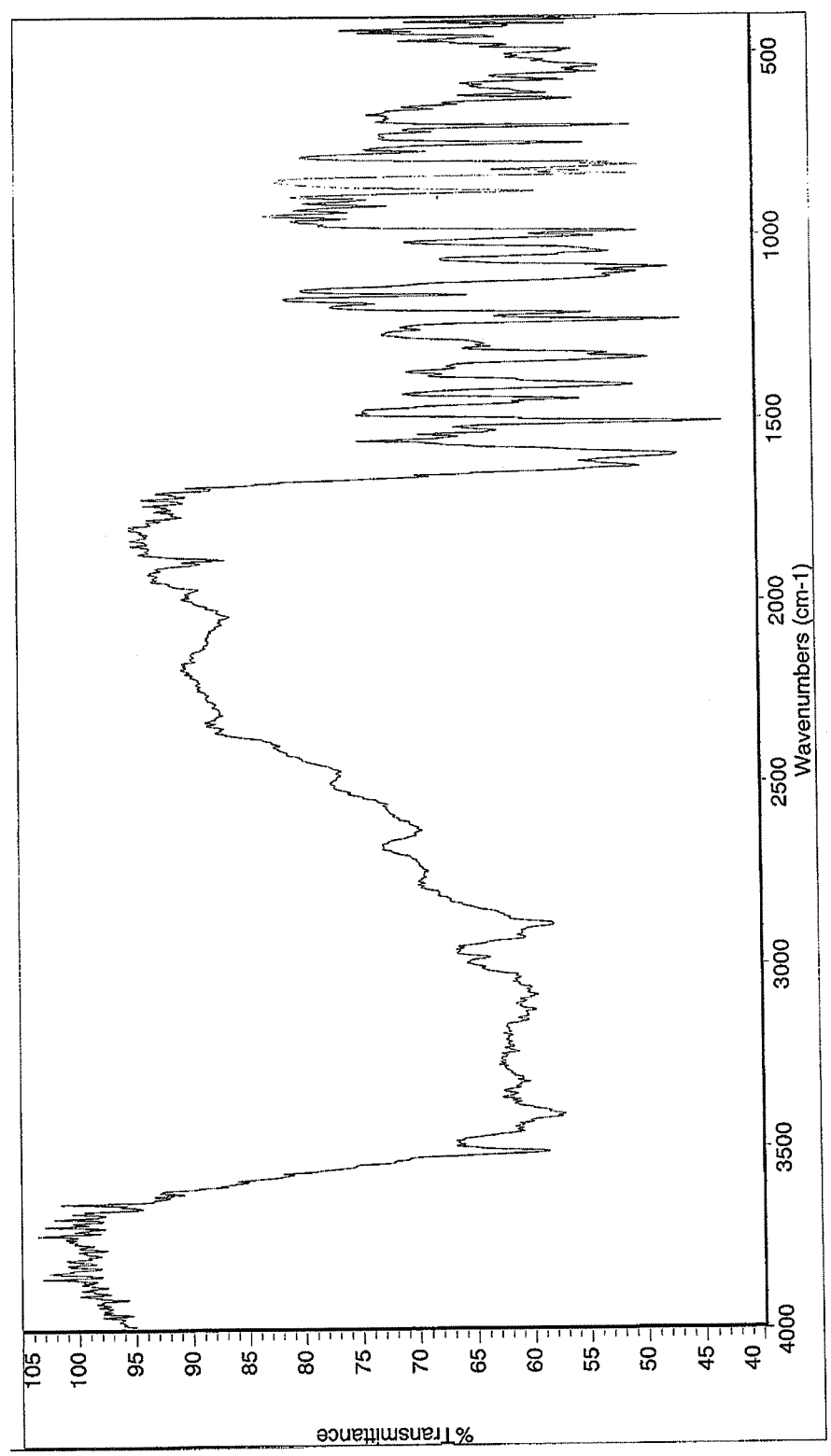

In other embodiments, a crystalline complex of canagliflozin and L-phenylalanine referred to as Form CS3 is characterized by an XRPD pattern substantially in accordance with FIG. 15. The XRPD pattern of Form CS3 shows that it is crystalline, and is different from amorphous canagliflozin and from L-phenylalanine. In some embodiments, the crystalline form of the compound is characterized by an XRPD pattern that includes two or more, three or more, four or more, or five or more peaks selected from peaks at 7.84, 8.52, 11.02, 11.76, 13.64, 14.18, 14.86, 15.21, 15.55, 15.73, 16.55, 17.11, 17.66, 18.81, 19.4, 19.72, 20.77, 21.36, 21.82, 22.19, 22.39, 22.6, 22.8, 23.23, 23.43, 23.67, 24.66, 25.2, 25.83, 26.56, 26.96, 27.72, 28.11, 28.64, 29.03, 29.77, 30.44, 30.7, 31.02, 31.47, 31.88 and 32.33 degrees 2θ (±0.1 degrees 2θ), wherein said XRPD pattern is made using CuK$_{α1}$ radiation. In some other embodiments, the crystalline form of the compound is characterized by an XRPD pattern that includes peaks (in degrees 2θ (±0.1 degrees 2θ)) as provided in FIG. 15 that are greater than 20 Cps. In other embodiments, the crystalline form of the compound is characterized by the XRPD peaks substantially in accordance with FIG. 15.

Figure 18:
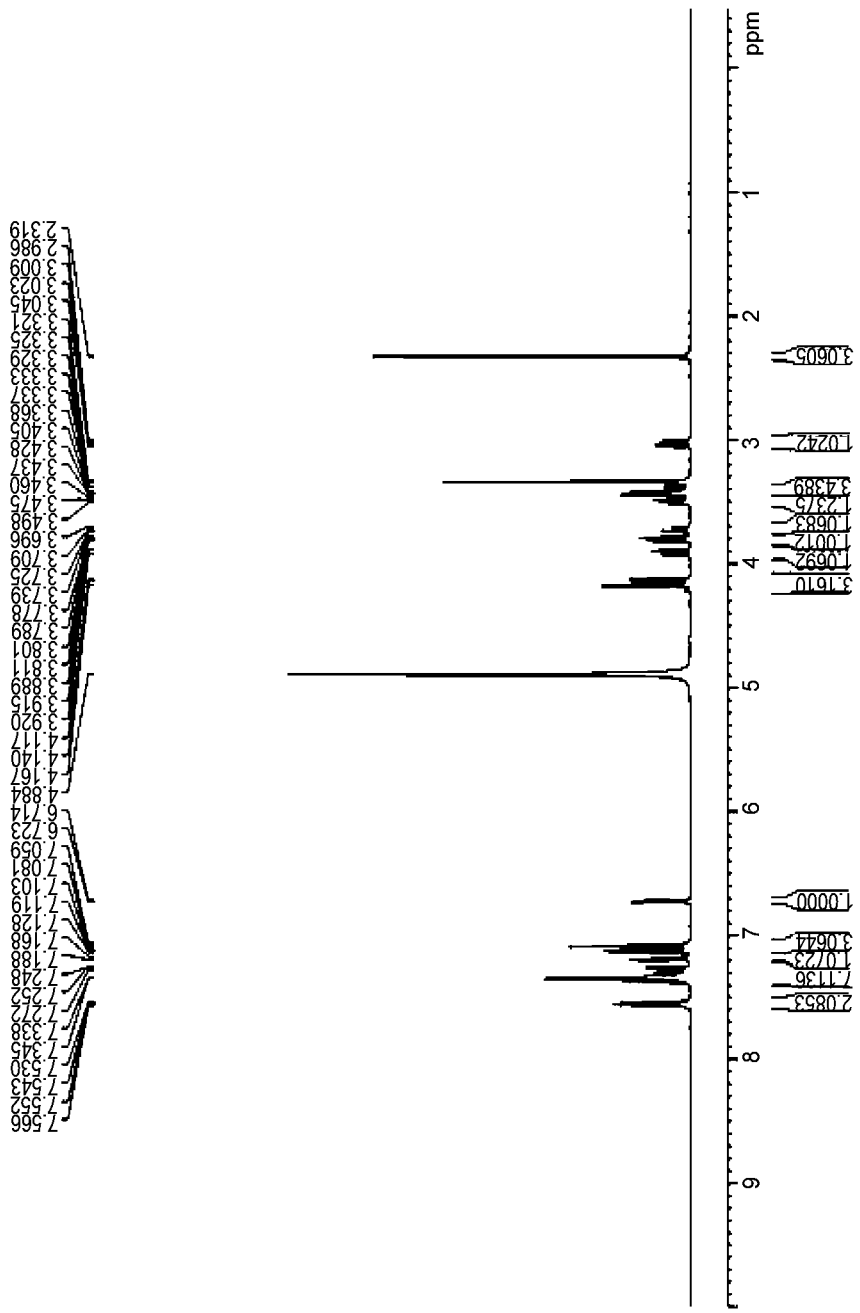
Figure 19:
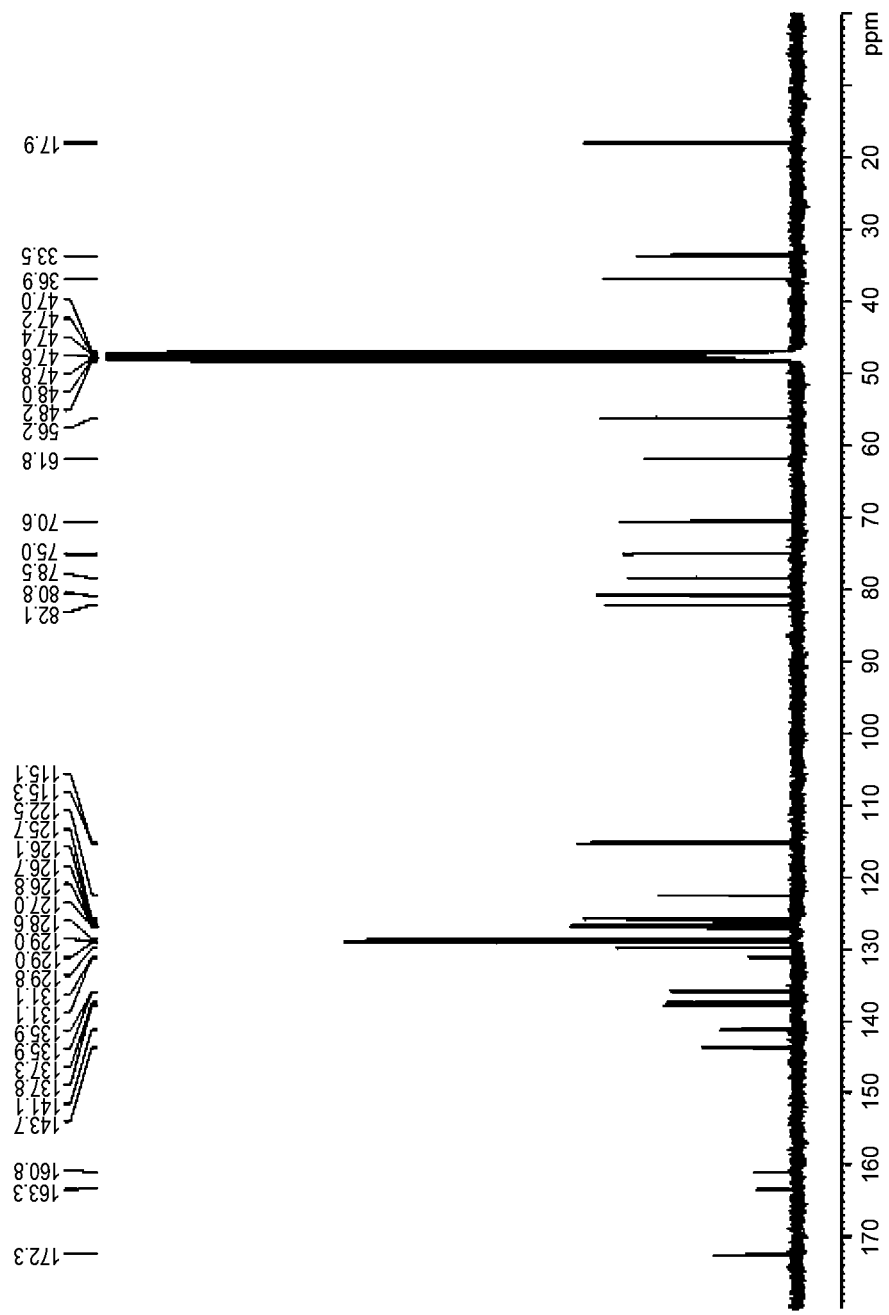
Figure 20:
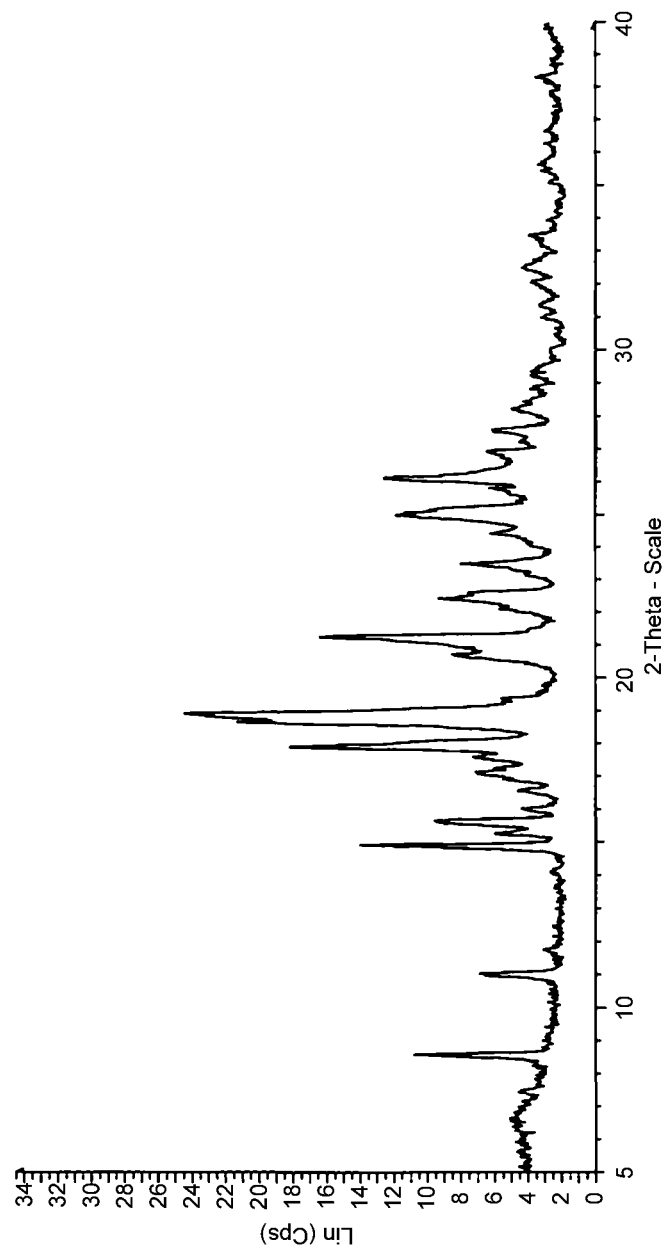
FIG. 20 provides the XRPD pattern of a 1:1 crystalline complex of canagliflozin and L-phenylalanine at 100° C. (Form CS3).

Crystallization of canagliflozin from aqueous EtOH in the presence of the natural amino acid L-phenylalanine provided solids that after drying in vacuo furnished a white solid (Form CS3) with melting starting at about 155° C. FIG. 18 is the $^1$H NMR spectrum of Form CS3 and shows that it comprises canagliflozin and L-phenylalanine in a 1:1 molar ratio.

Figure 17:
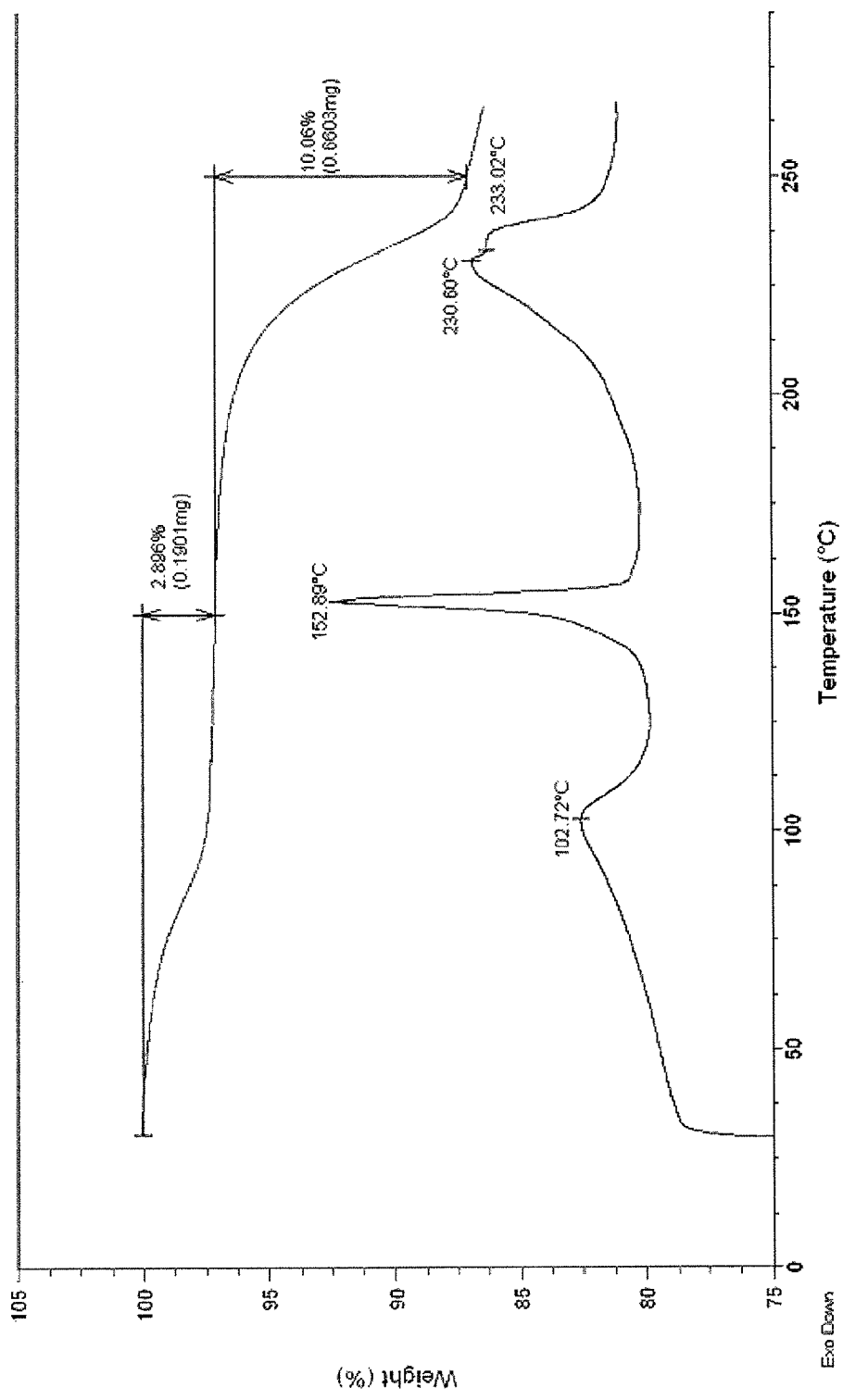
FIGS. 17, 18 and 19 provide the DSC and TGA traces, $^1$H NMR, and $^{13}$C NMR spectra, respectively of 1:1 crystalline complex of canagliflozin and L-phenylalanine (Form CS3).

Form CS3 has been further characterized using DSC/TGA and Karl Fischer titration. Karl Fischer titration analysis indicates that Form CS3 is a monohydrate. DSC analysis shows three endothermic transitions at about 105° C., 153° C. and 230° C. TGA analysis shows a mass loss due to dehydration from about 50° C. to 90° C. with a mass loss of 2.8%, which corresponds to the result obtained from Karl Fischer titration of about 3%. Form CS3 is non-hygroscopic and is stable as a monohydrate under laboratory environmental conditions. Dehydration, which is reversible, only occurs when the sample is exposed to a low humidity environment (e.g., less than about 10% RH). Under highly humid conditions, the form remains as a monohydrate. The DSC/TGA traces of crystalline complex Form CS3 of canagliflozin are in accordance with FIG. 17. The aforementioned physical stability characteristic of this embodiment makes the crystalline complex Form CS3 of canagliflozin a preferred solid form of canagliflozin of this invention.

Form CS3 has been further characterized at 100° by XRPD analysis to observe its crystalline nature following its dehydration. In some embodiments, the crystalline form of the complex of canagliflozin and L-phenylalanine following dehydration at 100° C. is characterized by a XRPD pattern that includes two or more, three or more, four or more, or five or more peaks selected from peaks at 7.41, 8.53, 10.98, 11.72, 14.09, 14.87, 15.26, 15.60, 15.97, 16.55, 17.09, 17.56, 17.89, 18.73, 18.85, 19.31, 20.69, 21.22, 22.15, 22.44, 23.49, 24.12, 24.45, 25.00, 25.78, 26.10, 26.91, 27.56, 28.22, 28.88, 29.26, 29.44, 29.99, 31.00, 31.38, 32.06,32.52, 33.27, 33.48, 33.95, 35.11 and 35.67 degrees 2θ (±0.1 degrees 2θ), wherein said XRPD pattern is acquired using CuK$_{α1}$ radiation. In some other embodiments, the crystalline form of the compound is characterized at 100° C. by a XRPD pattern that includes peaks (in degrees 2θ (±0.1 degrees 2θ)) as provided in FIG. 20 that are greater than 20 Cps. In other embodiments, the crystalline form of the compound is characterized at 100° C. by the XRPD peaks substantially in accordance with FIG. 20.

The results of XRPD analyses shows that the XRPD pattern acquired for Form CS3 at 100° C. (FIG. 20) is essentially the same as the XRPD pattern acquired at 25° C. (FIG. 15). Thus, from the XRPD patterns acquired at 25° C. and 100° C., it can be reasonably concluded that although Form CS3 is a monohydrate under ambient conditions (such as in an analytical chemistry laboratory), it can also exist as an anhydrate at low humidity, such as less than about 10% RH, and at temperatures higher than ambient temperature.

Figure 21:
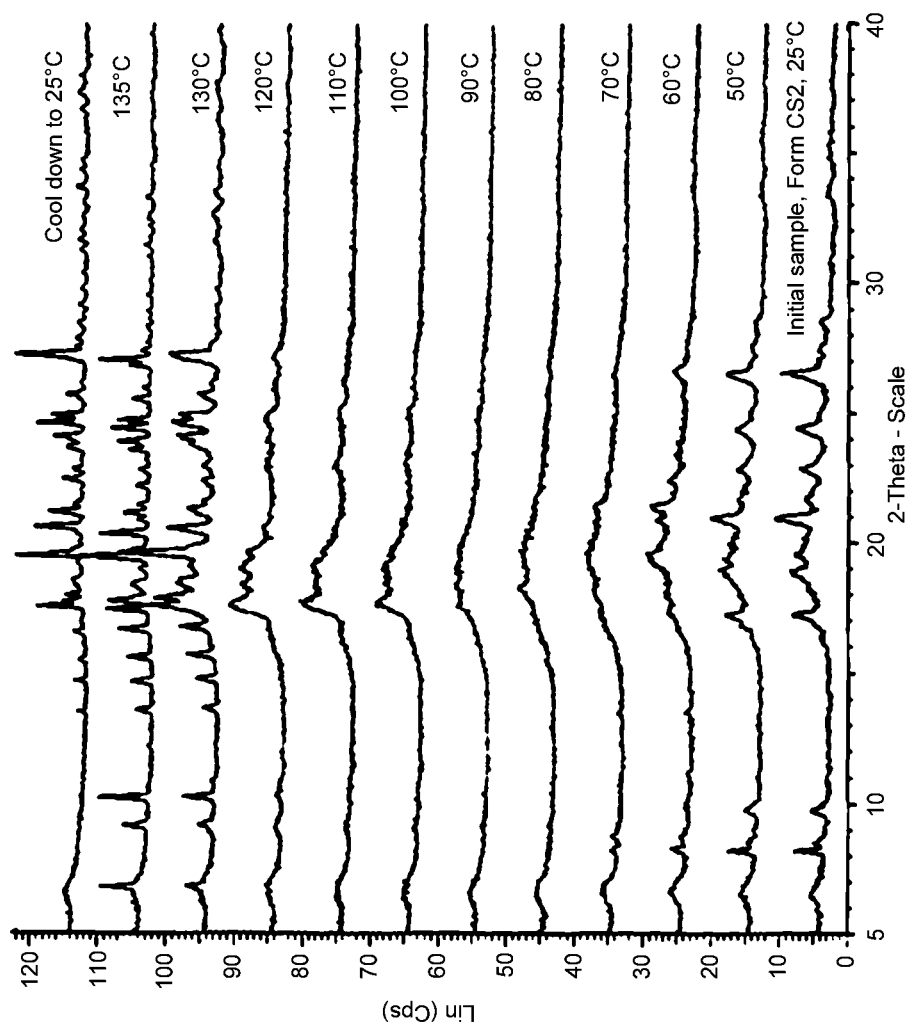
FIG. 21 provides a series of XRPD patterns of a 1:1 crystalline complex of canagliflozin with D-proline at different temperatures.

The inventors have unexpectedly discovered that when the 1:1 canagliflozin D-proline complex Form CS2, and other 1:1 canagliflozin D-proline complexes, is heated from 25° C. to 135° C. with a heating rate of 10° C./min, the form can be converted to a new form, as indicated by XRPD analysis. Further, the results of a HSM experiment and a series of XRPD analyses at different temperatures show that the canagliflozin D-proline complex undergoes a melting, or partial melting phenomenon, followed by a high temperature recrystallization event to generate the new form. The melting and recrystallization events occurred above 110° C. and were complete by 130° C. to 135° C. Upon reaching 135° C. the new and highly crystalline form was created, which retained the same XRPD pattern when cooled to room temperature. Accordingly, a new crystalline form can be prepared when a canagliflozin D-proline complex is heated to more than 125° C. and the new form is referred to as Form CS4. XRPD data collected over the course of the conversion process (from Form CS2 to Form CS4) is shown in FIG. 21.

Figure 10:
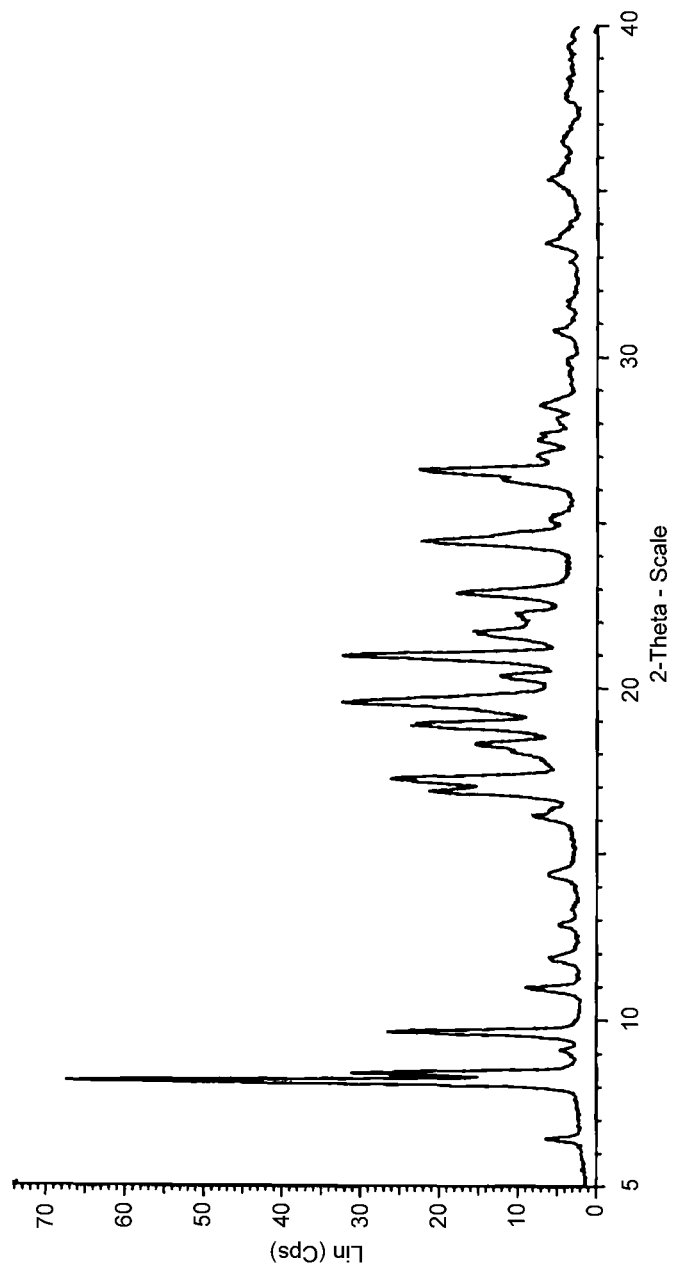
FIGS. 10 and 11 provide the XRPD pattern and IR spectrum, respectively, of an EtOH solvate of a 1:1 crystalline complex of canagliflozin with D-proline (Form CS2).
Figure 11:
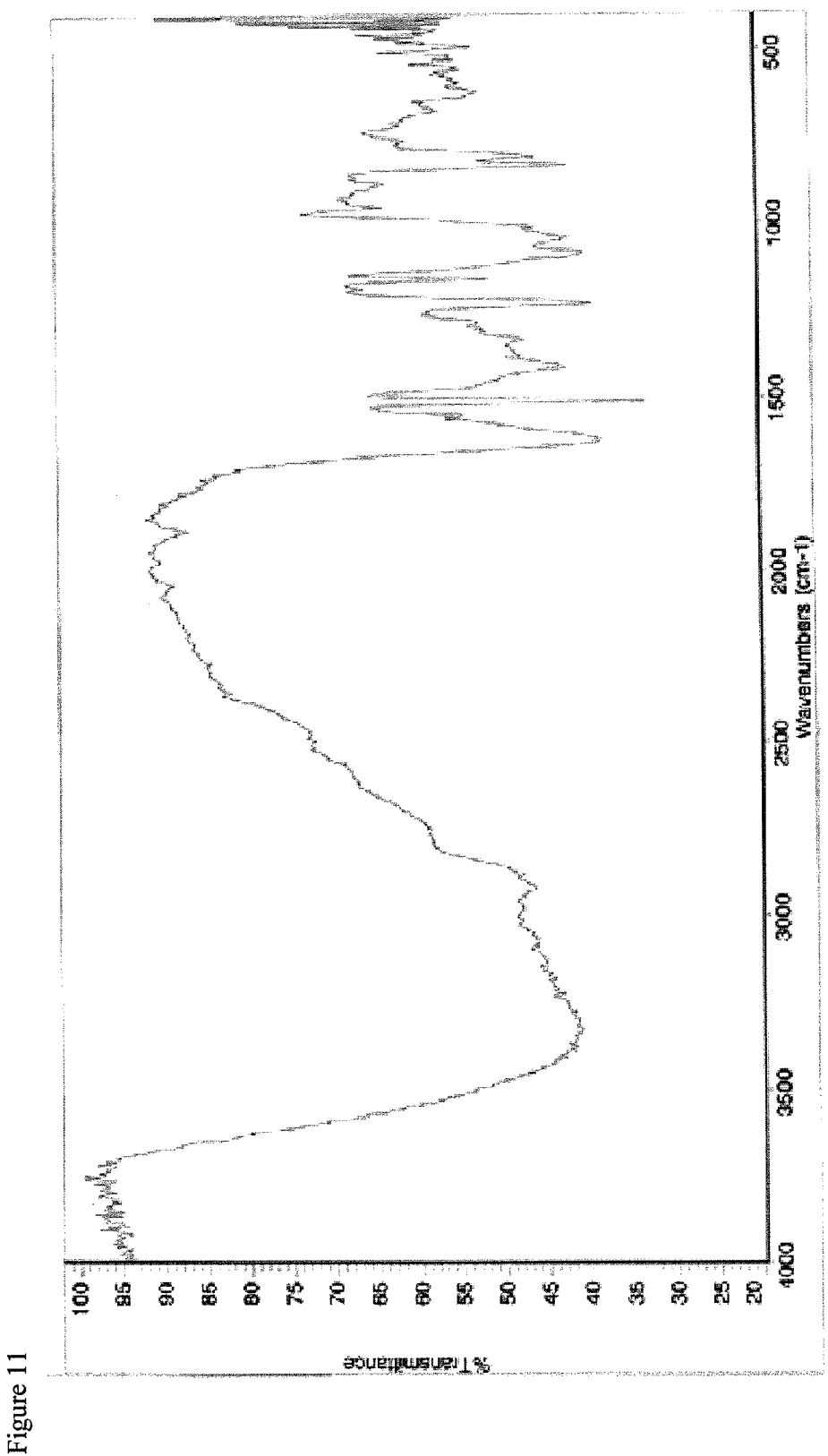
Figure 22:
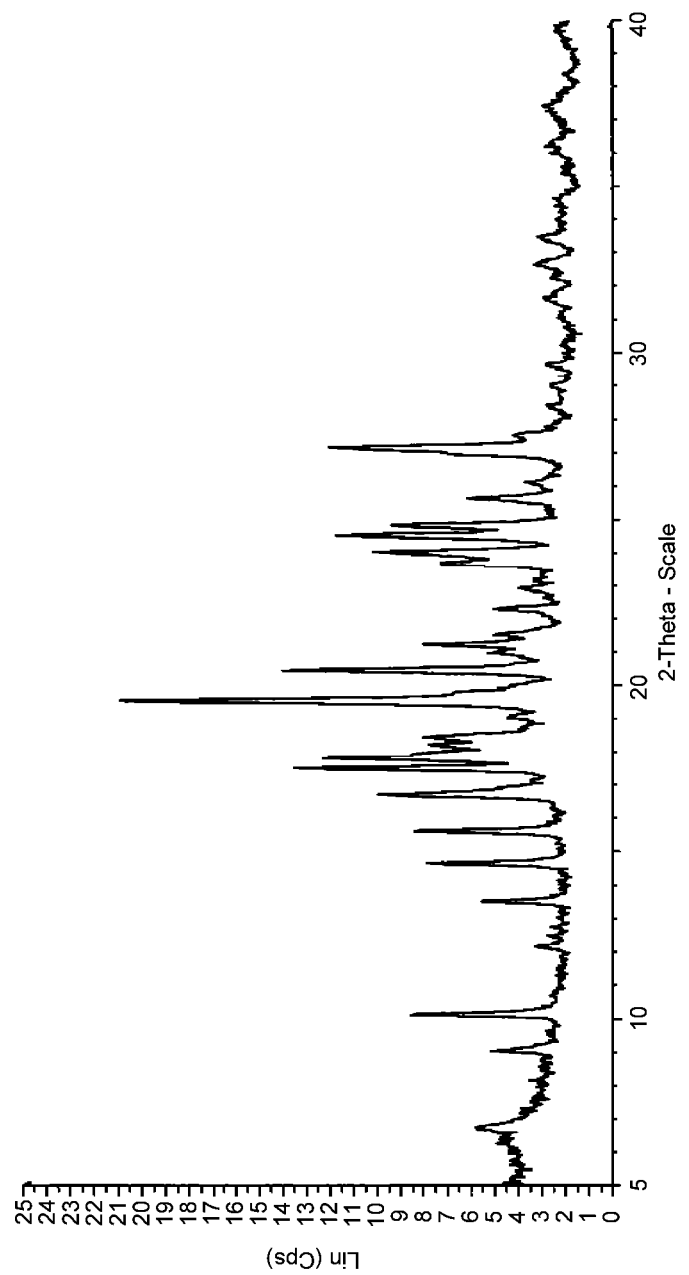
FIG. 22 provides the XRPD pattern of a 1:1 crystalline complex of canagliflozin with D-proline (Form CS4).

In some embodiments, the canagliflozin D-proline complex Form CS4 is further characterized by XRPD analysis at 135° C. FIG. 22 shows that the XRPD pattern of canagliflozin D-proline complex acquired at 135° C. is substantially different from the XRPD pattern of Form CS2 (FIG. 10).

In some embodiments, the crystalline form Form CS4 is characterized by an XRPD pattern that includes two or more, three or more, four or more, or five or more peaks selected from peaks at 6.74, 9.03, 10.11, 12.13, 12.50, 13.50, 14.64, 15.61, 16.69, 17.48, 17.80, 18.21, 18.44, 19.05, 19.54, 20.46, 20.98, 21.23, 21.53, 22.29, 22.91, 23.70, 24.03, 24.54, 24.85, 25.65, 26.14, 27.17, 27.53, 28.40, 29.02, 29.68, 31.13, 31.64, 31.79, 32.30, 32.67, 33.45, 34.60, 35.48, 36.34 and 37.46 degrees 2θ (±0.1 degrees 2θ), wherein said XRPD pattern is made using CuK$_{α1}$ radiation. In some other embodiments, the crystalline form of the compound is characterized by an XRPD pattern that includes peaks (in degrees 2θ (±0.1 degrees 2θ)) as provided in FIG. 22 that are greater than 20 Cps. In other embodiments, the crystalline form of the compound is characterized by some or all the XRPD peaks substantially in accordance with FIG. 22.

Form CS4 that was handled at ambient temperature has been further characterized using DSC/TGA. DSC analysis showed an endothermic transition with peak maximum at about 143° C. TGA analysis showed there was no significant mass loss. Thus, Form CS4 is a non-hygroscopic and anhydrous material under ambient conditions.

Figure 23:
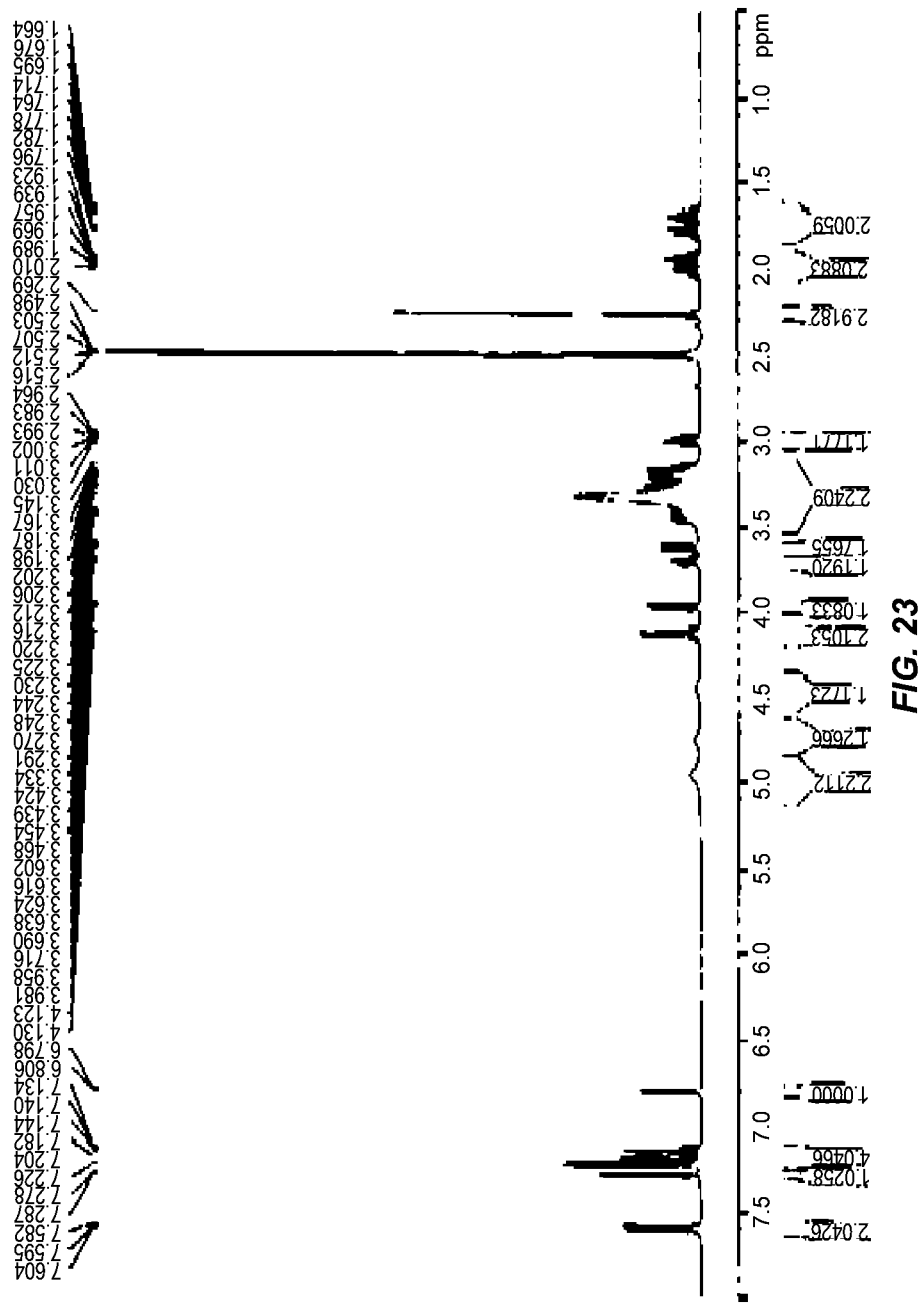
FIG. 23 provides the $^1$H NMR spectrum of a 1:1 crystalline complex of canagliflozin with D-proline (Form CS4).
Figure 24:
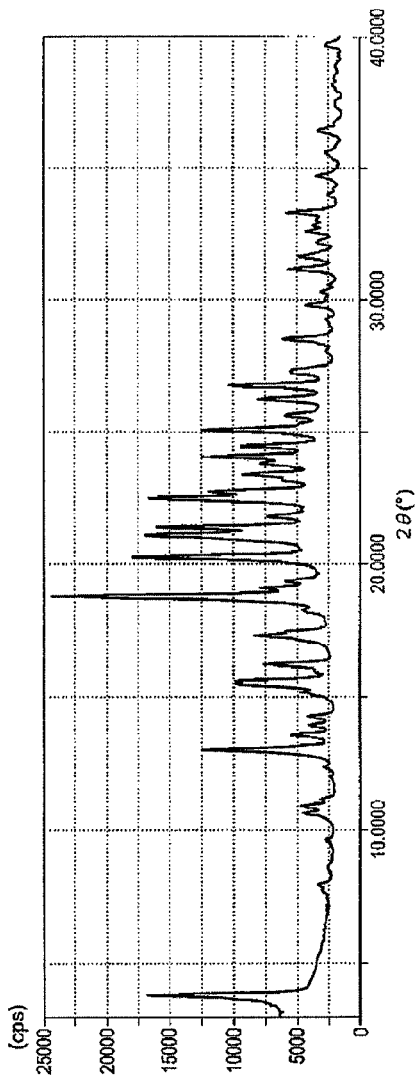
FIGS. 24 and 25 show previously disclosed XRPD patterns of crystalline forms of canagliflozin.
Figure 25:
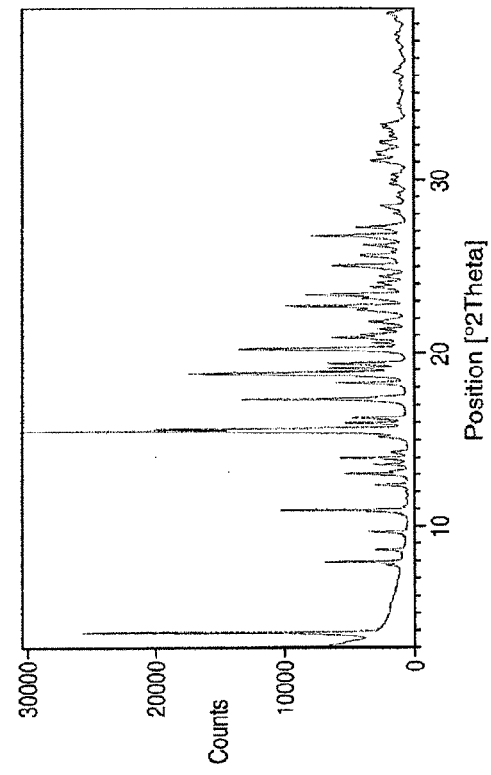

$^1$HNMR spectroscopic analysis of Form CS4 shows that it comprises canagliflozin with D-proline in a 1:1 molar ratio. FIG. 23 is the $^1$H NMR spectroscopic analysis of Form CS4 and it shows that Form CS4 comprises canagliflozin with D-proline in a 1:1 molar ratio.

Inventors have further discovered that heating Form CS4 can convert it to another form, CS5, with a DSC peak maximum melting point of 153° C.

Figure 2:
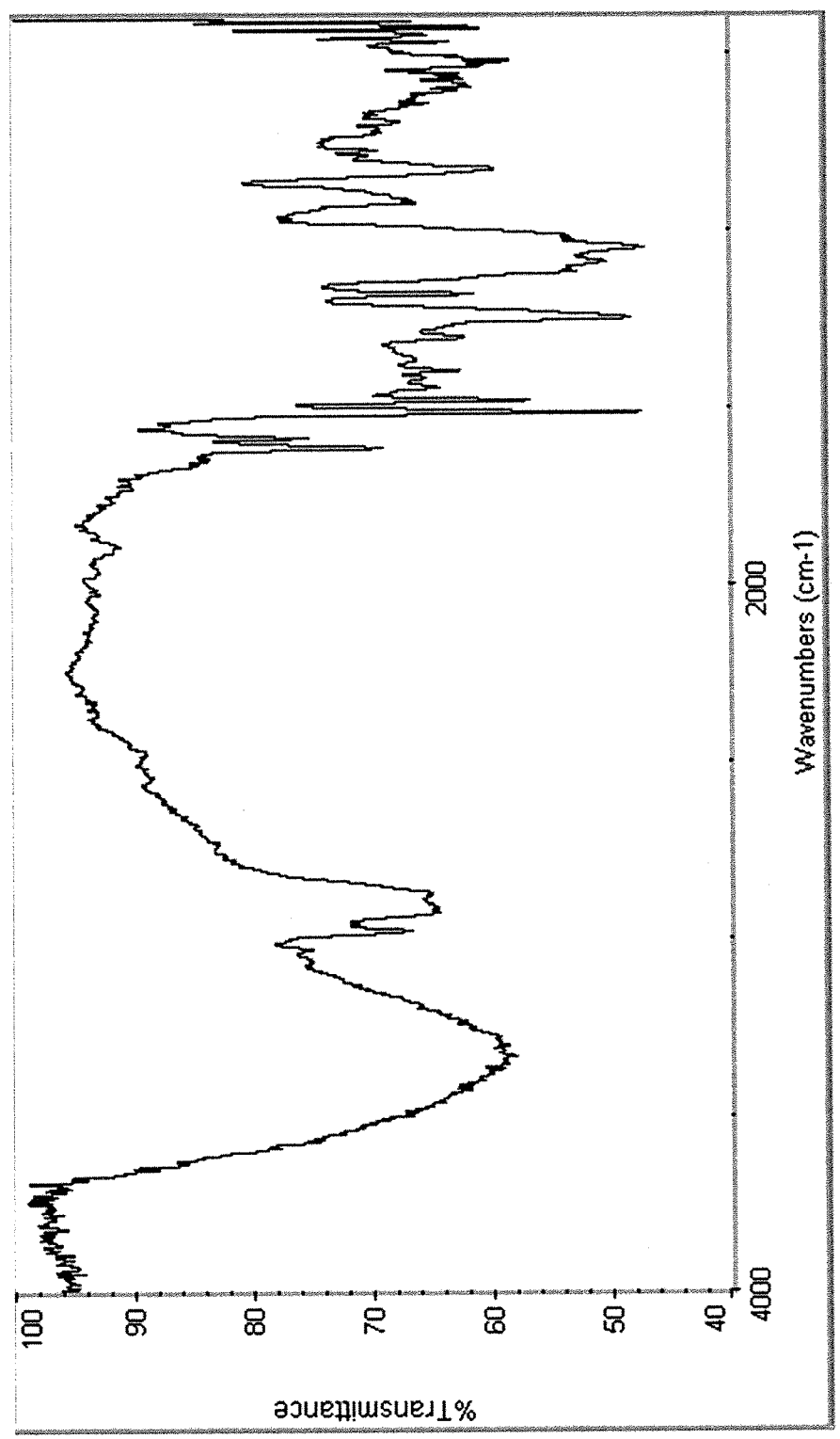

Table 2 shows the XRPD peaks of the crystalline complex Forms CS1 to CS4 of the present invention, respectively.

mL of n-heptane. The mixture was filtered and the resulting solids were dried in a vacuum oven to give 1.6 g of amorphous dapagliflozin as a white solid. The XRPD pattern and IR spectrum of the amorphous product is shown in FIGS. 1 and 2.

Example 2

Preparation of Amorphous Canagliflozin

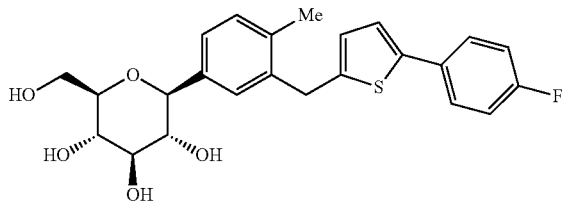 [SMILES: Cc1ccc([C@@H]2O[C@H](CO)[C@@H](O)[C@H](O)[C@H]2O)cc1Cc1ccc(-c2ccc(F)cc2)s1]

Canagliflozin (0.3 g, 0.67 mmol) was dissolved in 3 mL of toluene with heating. The resulting solution was added to 30 mL of n-heptane. The mixture was filtered and the resulting solids were dried in a vacuum oven to give 0.2 g of amorphous

TABLE 2

| Form | XRPD pattern data of crystalline complex forms of canagliflozin 2-Theta ° | | | | | | | | | | | | | |
|---|---|---|---|---|---|---|---|---|---|---|---|---|---|---|
| CS1 | 8.92 | 9.47 | 10.29 | 10.9 | 11.38 | 12.63 | 13.18 | 14.57 | 15.4 | 16.08 | 17.02 | 17.69 | 17.9 | 18.62 |
|  | 19.06 | 19.89 | 20.28 | 20.83 | 21.23 | 21.85 | 22.56 | 22.95 | 23.44 | 24.11 | 24.57 | 25.48 | 25.91 | 26.84 |
|  | 27.7 | 28.1 | 28.75 | 29.84 | 30.41 | 30.86 | 31.3 | 31.63 | 32.21 | 33.67 | 34.47 | 35.1 | 35.91 | 36.37 |
| CS2 | 8.13 | 8.4 | 9.08 | 9.63 | 10.95 | 11.85 | 12.88 | 13.33 | 14.37 | 16.12 | 16.86 | 17.23 | 18.02 | 18.29 |
|  | 18.88 | 19.56 | 20.35 | 20.97 | 21.67 | 22.22 | 22.89 | 24.45 | 25.14 | 26.3 | 26.59 | 27.06 | 27.54 | 28.17 |
|  | 28.58 | 29.9 | 30.79 | 31.69 | 32.89 | 33.45 | 33.7 | 34.04 | 35.38 | 36.47 | 37 | 37.93 | 38.43 | 39.37 |
| CS3 | 7.84 | 8.52 | 11.02 | 11.76 | 13.64 | 14.18 | 14.86 | 15.21 | 15.55 | 15.73 | 16.55 | 17.11 | 17.66 | 18.81 |
|  | 19.4 | 19.72 | 20.77 | 21.36 | 21.82 | 22.19 | 22.39 | 22.6 | 22.8 | 23.23 | 23.43 | 23.67 | 24.66 | 25.2 |
|  | 25.83 | 26.56 | 26.96 | 27.72 | 28.11 | 28.64 | 29.03 | 29.77 | 30.44 | 30.7 | 31.02 | 31.47 | 31.88 | 32.33 |
| CS3 (at 135° C.) | 7.41 | 8.53 | 10.98 | 11.72 | 14.09 | 14.87 | 15.26 | 15.60 | 15.97 | 16.55 | 17.09 | 17.56 | 17.89 | 18.73 |
|  | 18.85 | 19.31 | 20.69 | 21.22 | 22.15 | 22.44 | 23.49 | 24.12 | 24.45 | 25.00 | 25.78 | 26.10 | 26.91 | 27.56 |
|  | 28.22 | 28.88 | 29.26 | 29.44 | 29.99 | 31.00 | 31.38 | 32.06 | 32.52 | 33.27 | 33.48 | 33.95 | 35.11 | 35.67 |
| CS4 | 6.74 | 9.03 | 10.11 | 12.13 | 12.50 | 13.50 | 14.64 | 15.61 | 16.69 | 17.48 | 17.80 | 18.21 | 18.44 | 19.05 |
|  | 19.54 | 20.46 | 20.98 | 21.23 | 21.53 | 22.29 | 22.91 | 23.70 | 24.03 | 24.54 | 24.85 | 25.65 | 26.14 | 27.17 |
|  | 27.53 | 28.40 | 29.02 | 29.68 | 31.13 | 31.64 | 31.79 | 32.30 | 32.67 | 33.45 | 34.60 | 35.48 | 36.34 | 37.46 |

Of the embodiments described, the crystalline complexes Form CS1 and Form CS3 of canagliflozin are the more preferred solid forms of canagliflozin of this invention, and the crystalline complex Form CS1 is the most preferred solid form of canagliflozin of this invention.

EXAMPLES

The following examples are provided to further illustrate, but not to limit this invention.

Example 1

Preparation of Amorphous Dapagliflozin

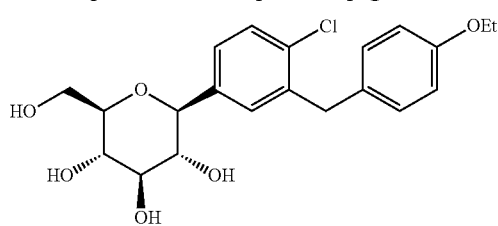

Figure 3:
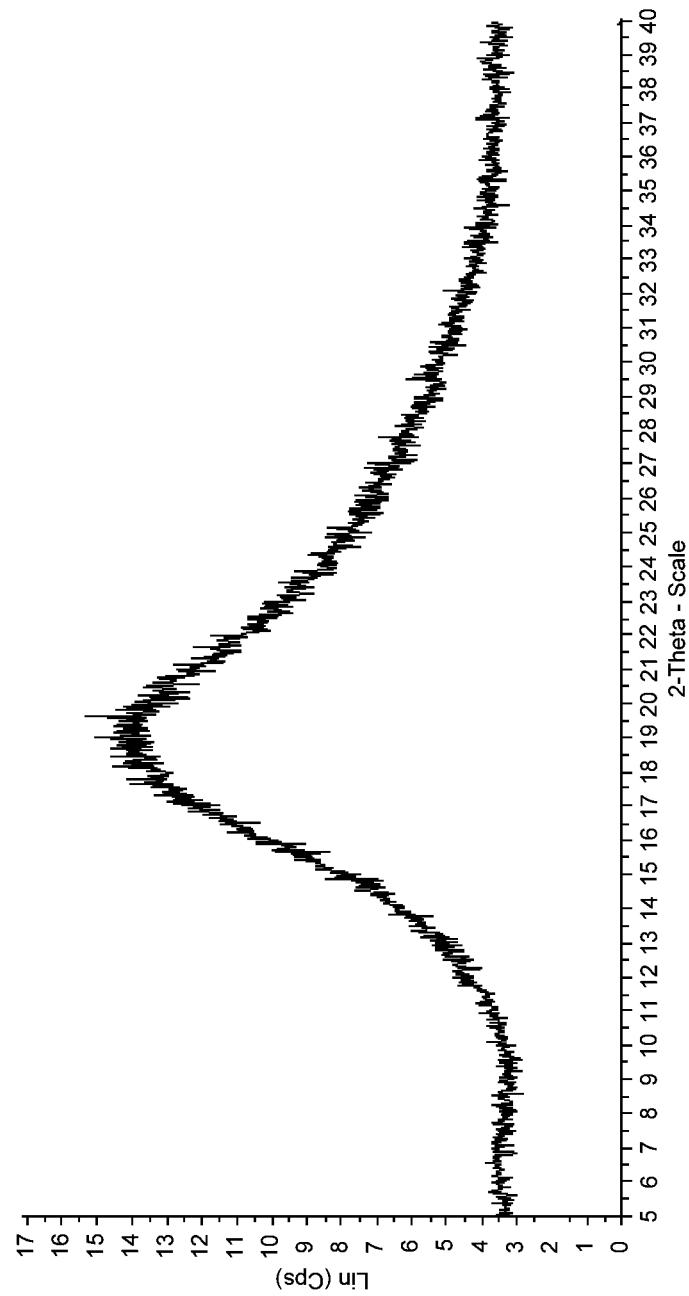
FIGS. 3 and 4 provide the XRPD pattern and IR spectrum, respectively, of amorphous canagliflozin.
Figure 4:
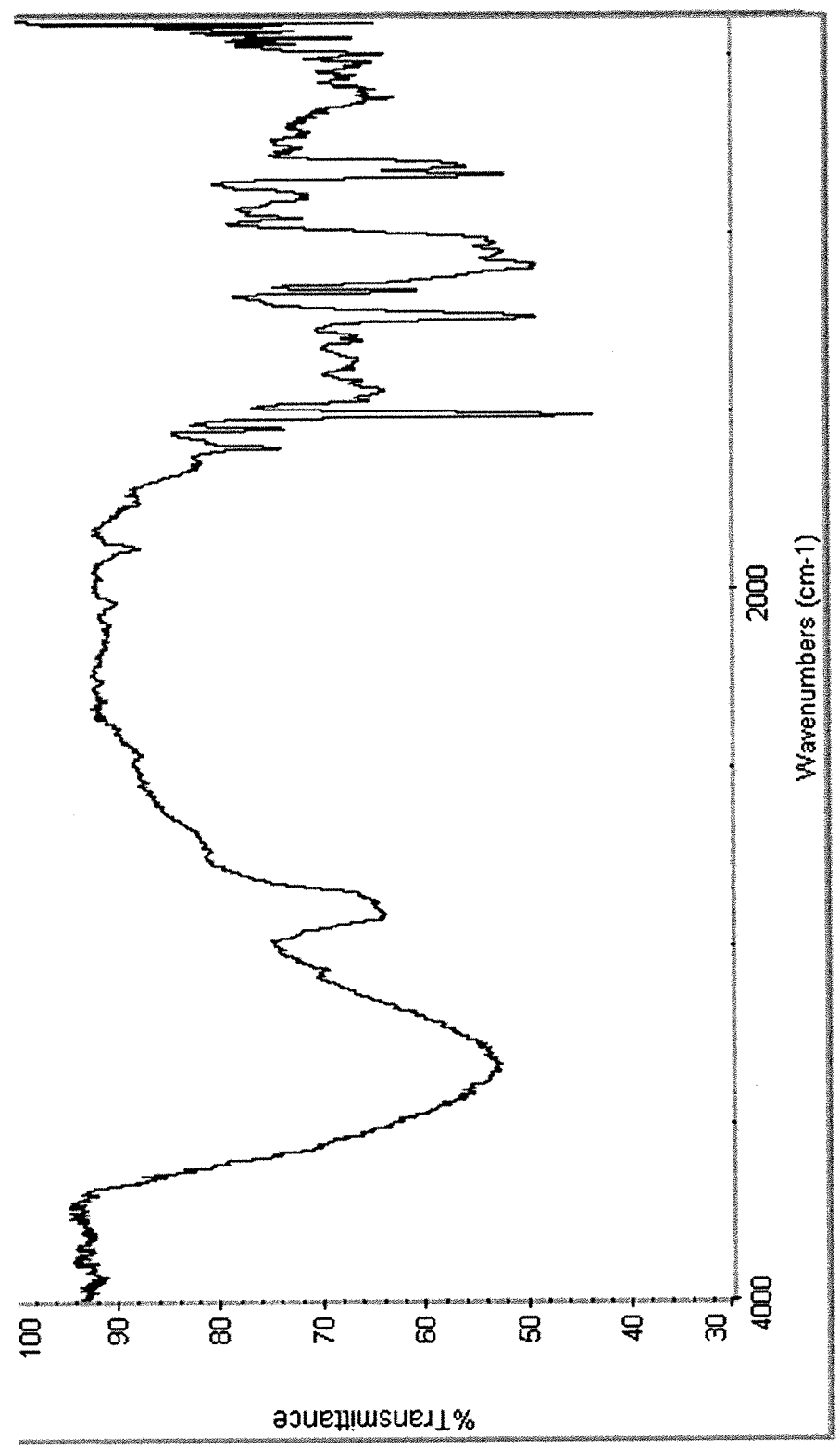
Figure 5:
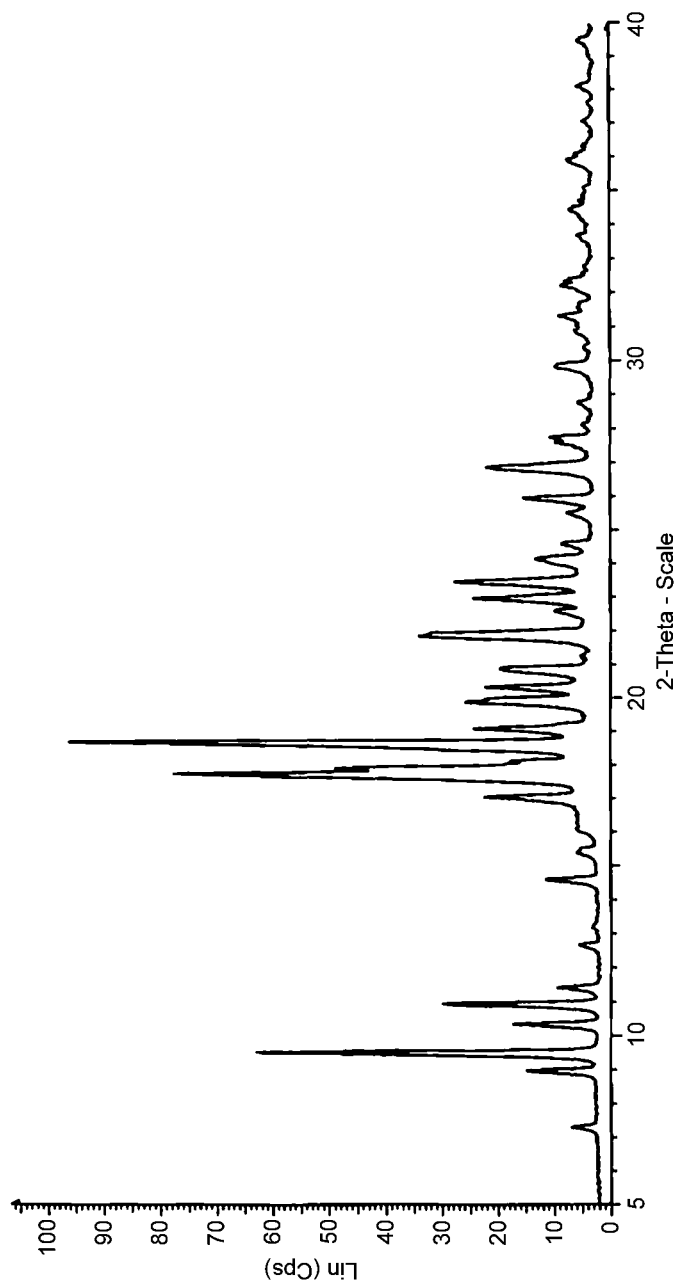
FIGS. 5 and 6 provide the XRPD pattern and IR spectrum, respectively, of a 1:1 crystalline complex of canagliflozin with L-proline (Form CS1).
Figure 6:
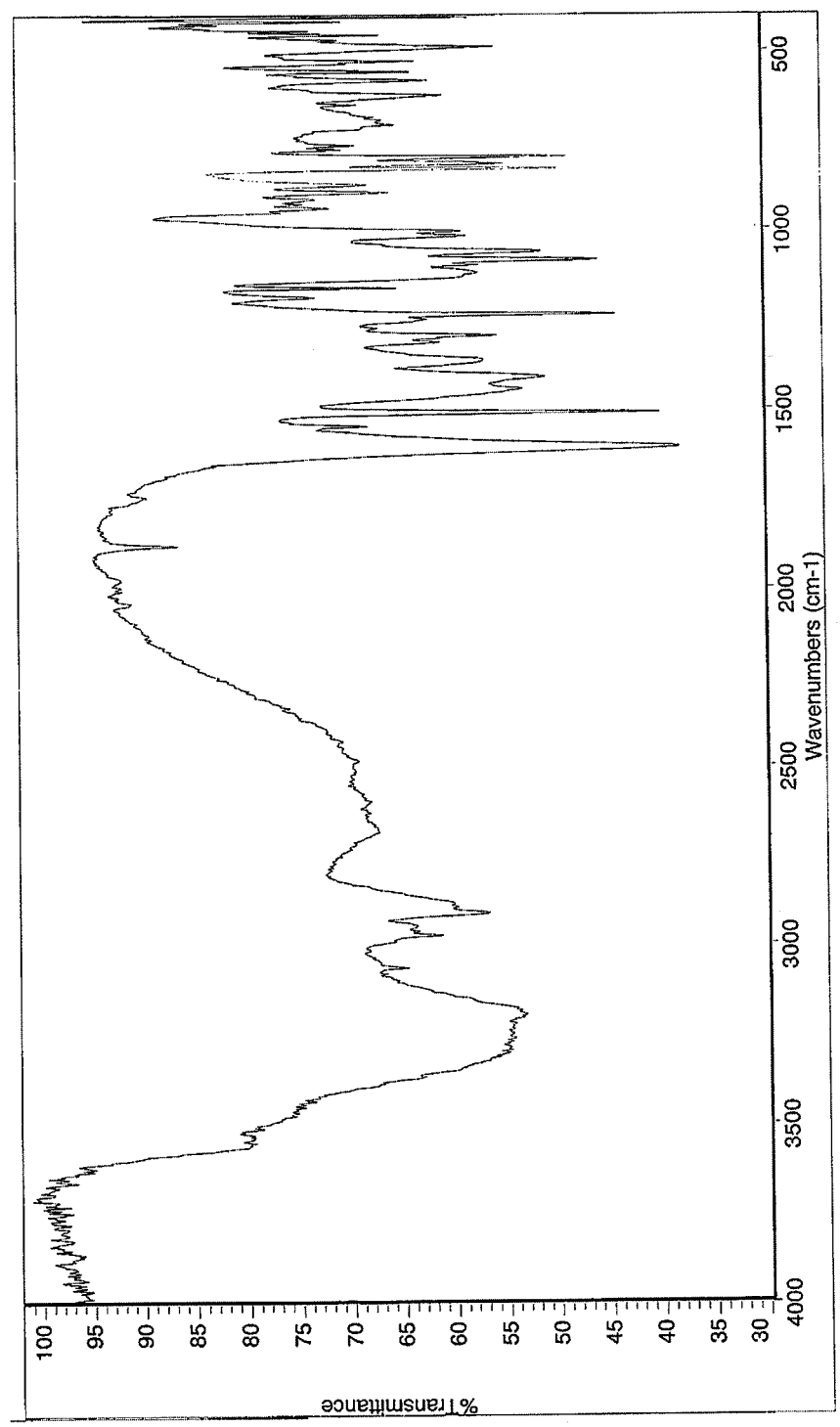

Dapagliflozin (1.7 g, 4.2 mmol) was dissolved in 10 mL of toluene with heating. The resulting solution was added to 40 canagliflozin as a white solid. The XRPD pattern and IR spectrum of the amorphous product is shown in FIGS. 3 and 4.

Example 3

Preparation of A 1:1 Crystalline Complex of Canagliflozin And L-Proline (Form CS1)

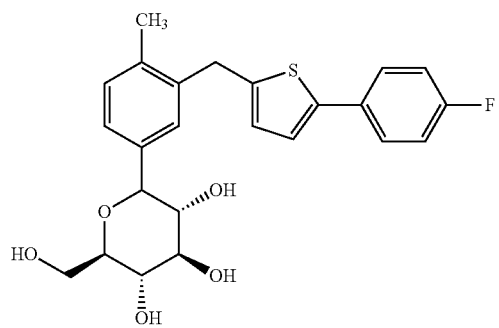

-continued

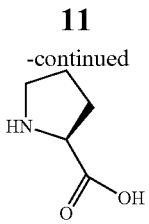

A solution of canagliflozin (0.3 g, 0.67 mmol), L-proline (0.17 g, 1.5 mmol), and 5 mL of 95% EtOH aq. was heated and dissolved. The solution was cooled slowly to room temperature. The solution was filtered and the resulting solids were dried under vacuum oven to give 0.3 g of a white solid. The XRPD pattern, IR spectrum, DSC and TGA traces, $^1$H NMR and $^{13}$C NMR spectra of the crystalline complex are shown in FIGS. 5, 6, 7, 8 and 9.

Example 4

Preparation of An EtOH Solvate of A 1:1 Crystalline Complex of Canagliflozin With D-Proline (Form CS2)

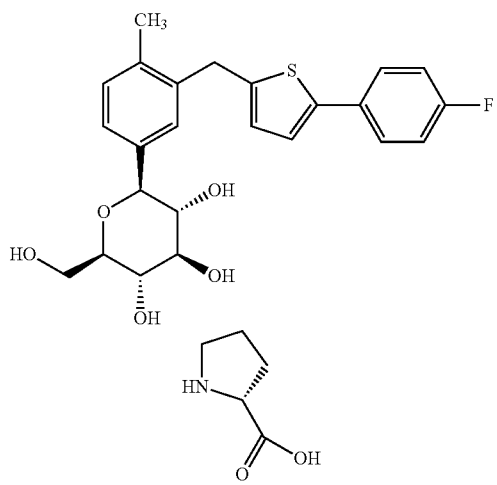

Canagliflozin (0.3 g, 0.67 mmol) and D-proline (0.09 g, 0.8 mmol) were dissolved in 5 mL of 95% aqueous EtOH by heating. The solution was cooled slowly to room temperature and the mixture was filtered and the resulting solids were dried in a vacuum oven to give 0.32 g of the crystalline complex as a white solid. The XRPD pattern, IR spectrum, DSC and TGA traces, $^1$H NMR and $^{13}$C NMR spectra of the crystalline complex are shown in FIGS. 10, 11, 12, 13 and 14.

Example 5

Preparation of A 1:1 Crystalline Complex of Canagliflozin And L-Phenylalanine (Form CS3)

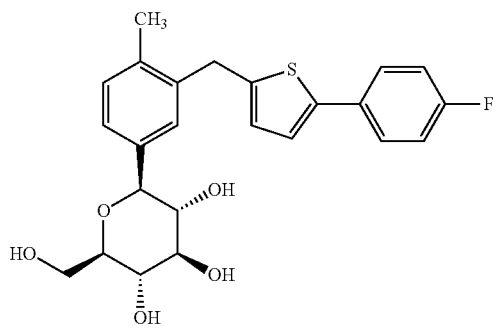

-continued

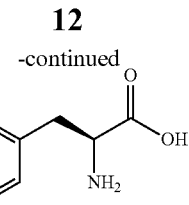

Canagliflozin (0.4 g, 0.9 mmol) and L-phenylalanine (0.33 g, 2 mmol) were dissolved in a mixture of 3.2 mL of absolute EtOH and 3.2 mL of H$_2$O with heating. The solution was cooled slowly to room temperature and the resulting mixture was filtered. The resulting solids were dried in a vacuum oven to give 0.52 g of the complex as a white solid. The XRPD pattern, IR spectrum, DSC and TGA traces, $^1$H NMR and $^{13}$C NMR spectra of the crystalline complex are shown in FIGS. 15, 16, 17, 18 and 19.

Example 6

Preparation of A 1:1 Crystalline Complex of Canagliflozin With D-Proline (Form CS4)

0.2 grams of a 1:1 canagliflozin D-proline complex was heated from 25° C. to 135° C. with a heating rate of 10° C./min, and was then cooled to ambient temperature. XRPD patterns at different temperatures during the heating process can be seen in FIG. 21. $^1$H NMR spectroscopic analysis (see FIG. 23) of the resulting crystalline form showed that this was a 1:1 crystalline complex of canagliflozin with D-proline.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A crystalline complex form of canagliflozin selected from the group consisting of Form CS2, CS3, CS4 and CS5, wherein said crystalline form is substantially free of other crystalline forms.

2. A crystalline complex form of claim 1, having Form CS2.

3. A crystalline complex form of claim 1, having Form CS3.

4. A crystalline complex form of claim 1, having Form CS4.

5. A crystalline complex form of claim 1, having Form CS5.

6. A composition comprising a pharmaceutically acceptable excipient and a crystalline complex form of canagliflozin having a form selected from the group consisting of Form CS2, Form CS3, Form CS4 and Form CS5.

7. A composition of claim 6, wherein said crystalline complex form of canagliflozin is Form CS2.

8. A composition of claim 6, wherein said crystalline complex form of canagliflozin is Form CS3.

9. A composition of claim 6, wherein said crystalline complex form of canagliflozin is Form CS4.

10. A composition of claim 6, wherein said crystalline complex form of canagliflozin is Form CS5.

* * * * *